(12) United States Patent
Liu et al.

(10) Patent No.: US 8,563,267 B2
(45) Date of Patent: Oct. 22, 2013

(54) LYCOGEN EXTRACT, COMPOSITION THEREOF AND METHOD FOR THE TREATMENT USING THE SAME

(75) Inventors: Wen-Sheng Liu, Kaohsiung (TW); Fu-Hsin Chang, Kaohsiung (TW); Ya-Wen Tsai, Kaohsiung (TW)

(73) Assignee: Asia-Pacific Beiotech Developing, Inc., Kaohsiung (TW)

( * ) Notice: Subject to any disclaimer, the term of this patent is extended or adjusted under 35 U.S.C. 154(b) by 98 days.

(21) Appl. No.: 13/187,857

(22) Filed: Jul. 21, 2011

(65) Prior Publication Data
US 2012/0027707 A1    Feb. 2, 2012

(30) Foreign Application Priority Data
Jul. 22, 2010  (TW) ............... 99124072 A

(51) Int. Cl.
*C12N 9/00* (2006.01)
(52) U.S. Cl.
USPC ............ 435/62; 435/67; 435/252.3; 435/23.2
(58) Field of Classification Search
USPC .......................................................... 424/62
See application file for complete search history.

(56) References Cited

U.S. PATENT DOCUMENTS

2003/0003528 A1* 1/2003 Brzostowicz et al. .......... 435/67
2004/0219629 A1* 11/2004 Cheng et al. .................... 435/67

OTHER PUBLICATIONS

Burgess et al., Possible dissociation of the heparin-binding.. Journal of Cell Biology, vol. 111, 2129-2138, 1990.*
Lin et al., Structure-Function Relationship: Biochemistry, vol. 14, 1559-1563, 1975.*
Gu et al.,Optimization of carotenoids extraction from Rhodobacter spheroids, LWT 41, 1082-1088, 2008.*

* cited by examiner

*Primary Examiner* — Tekchand Saidha
*Assistant Examiner* — Rama P Ramanujam
(74) *Attorney, Agent, or Firm* — WPAT, P.C.; Anthony King

(57) ABSTRACT

A lycogen extract comprising active ingredient of $\zeta$-carotene, neurosporene, spheroidenone and/or methoxyneurosporene is described. A composition comprising the lycogen extract of the present invention and food scientific or pharmaceutical acceptable carrier is also presented. A method for the treatment of disease in need of the lycogen extract which comprises administering to a patient in need thereof a therapeutically effective amount of lycogen extract of the present invention is further described.

8 Claims, 23 Drawing Sheets

FIGURE 3A

```
                    10         20         30         40         50         60
SEQ ID NO:3  TCAGGAAAAGCTCCAGCCGGGCGGCGGGGACGCGGACGGCGAGCATCGGCATCAGGAG
             :::::::::::::::::::::::::::::::::::::::::::::::::::::::::::
SEQ ID NO:1  TCAGGAAAAGCTCCAGCCGGGCGGCGGGGACGCGGACGGCGAGCATCGGCATCAGGAG
                    70         80         90        100        110        120
SEQ ID NO:3  CGGCGAGCGGAAGCGATGCAGATCGAGGCCTGTGCACGCCGACCGTCTTCTGGCCGAA
             :::::::::::::::::::::::::::::::::::::::::::::::::::::::::::
SEQ ID NO:1  CGGCGAGCGGAAGCGATGCAGATCGAGGCCTGTGCACGCCGACCGTCTTCTGGCCGAA
                   130        140        150        160        170        180
SEQ ID NO:3  GACCGTCGTCTGACCATCGCGCGCGATAGAACGGCGCGTGAGCATCGACATCACCTG
             :::::::::::::::::::::::::::::::::::::::::::::::::::::::::::
SEQ ID NO:1  GACCGTCGTCTGACCATCGCGCGCGATAGAACGGCGCGTGAGCATCGACATCACCTG
                   190        200        210        220        230        240
SEQ ID NO:3  CCGCGGCCGTGTGCCCGGATCGGCGGCGTGTTGACGCTCGACCAGCCAGCCGAGCGGGC
             :::::::::::::::::::::::::::::::::::::::::::::::::::::::::::
SEQ ID NO:1  CCGCGGCCGTGTGCCCGGATCGGCGGCGTGTTGACGCTCGACCAGCCAGCCGAGCGGGC
                   250        260        270        280        290        300
SEQ ID NO:3  GAAGCGGGCTTCGGGCGGCGGCTGATCAGCCGCGCGGCGGTCGGCCGGGACATGGAG
             :::::::::::::::::::::::::::::::::::::::::::::::::::::::::::
SEQ ID NO:1  GAAGCGGGCTTCGGGCGGCGGCTGATCAGCCGCGCGGCGGTCGGCCGGGACATGGAG
                   310        320        330        340        350        360
SEQ ID NO:3  CCCGAGCTGAGCCGGGAGCCGTCGGCGCGGGTCGCGTGTAGAAGCAGGCCGGCCCGTC
             :::::::::::::::::::::::::::::::::::::::::::::::::::::::::::
SEQ ID NO:1  CCCGAGCTGAGCCGGGAGCCGTCGGCGCGGGTCGCGTGTAGAAGCAGGCCGGCCCGTC
                   370        380        390        400        410        420
SEQ ID NO:3  TGCCACCGGGTAGCGGCCCCAGGTCCAGAAACGGAAGTGGCCTCGAGCGCGGCCGTGCC
             :::::::::::::::::::::::::::::::::::::::::::::::::::::::::::
SEQ ID NO:1  TGCCACCGGGTAGCGGCCCCAGGTCCAGAAACGGAAGTGGCCTCGAGCGCGGCCGTGCC
                   430        440        450        460        470        480
SEQ ID NO:3  GAAATTGGCATCGAAATAGCCGTGCCGTGCCAGCGGTGGCCCTGCGTCAGATCGACCTC
             :::::::::::::::::::::::::::::::::::::::::::::::::::::::::::
SEQ ID NO:1  GAAATTGGCATCGAAATAGCCGTGCCGTGCCAGCGGTGGCCCTGCGTCAGATCGACCTC
```

FIGURE 3B

```
                 490        500        510        520        530        540
SEQ ID NO:3  GATGCCGCGGTGCGTTCGAAGGGGCGCCAGATGTGCGAGCCATCGTCCTTGACGGTCAC
             ::::::::::::::::::::::::::::::::::::::::::::::::::::::::::::
SEQ ID NO:1  GATGCCGCGGTGCGTACGAAGGGGCGCCAGATGTGCGAGCCATCGTCCTTGACGGTCAC
                 550        560        570        580        590        600
SEQ ID NO:3  CTCGACATCGGTGATCCCGGTGGGGTCAGCACGATCCGGCCCTTCACCGGCGAGACGAG
             ::::::::::::::::::::::::::::::::::::::::::::::::::::::::::::
SEQ ID NO:1  CTCGACATCGGTGATCCCGGTGGGGTCAGCACGATCCGGCCCTTCACCGGCGAGACGAG
                 610        620        630        640        650        660
SEQ ID NO:3  GGCGGCGAGGAGATCTCGTTCACCTCGACGATGAGCTGGGTGCCGGTCCAGTGCATCCG
             ::::::::::::::::::::::::::::::::::::::::::::::::::::::::::::
SEQ ID NO:1  GGCGGCGAGGAGATCTCGTTCACCTCGACGATGAGCTGGGTGCCGGTCCAGTGCATCCG
                 670        680        690        700        710        720
SEQ ID NO:3  CGAGGGCCCACGGTCAGCGTGTCCGGCTCTGCCGCAGCGCGGCG--GCCGCT--TCGGT
             :::::::::::::::::::::::::::::::::::::::::::::  :::::::  :::::
SEQ ID NO:1  CGAGGGCCCACGGTCAGCGTGTCCGGCTCTGCCGCAGCGCGGCGCGGCCGCCGTCGGT
                 730        740        750        760        770        780
SEQ ID NO:3  CATGGTGAAGCGCCCGCCGGGGCCGTAGGTCGCCACATTGAGGCAGCAGTGGTTCTGCGG
             ::::::::::::::::::::::::::::::::::::::::::::::::::::::::::::
SEQ ID NO:1  CATGGTGAAGCGCCCGCCGGGGCCGTAGGTCGCCACATTGAGGCAGCAGTGGTTCTGCGG
                 790        800        810        820        830        840
SEQ ID NO:3  CTCCTTCCGGCCCGACCAGCGATACCAGGGCGAGAAGACGGAGCCGATGAAGCCGATCAC
             ::::::::::::::::::::::::::::::::::::::::::::::::::::::::::::
SEQ ID NO:1  CTCCTTCCGGCCCGACCAGCGATACCAGGGCGAGAAGACGGAGCCGATGAAGCCGATCAC
```

FIGURE 4

```
                  10        20        30        40        50        60
SEQ ID NO:4   VIGFIGSVFSPWYIRSGRKEPQNICCLNVATYGPGGHFTNETTIHAA-AALHQSPDTLTVG
              ::::::::::::::::::::::::::::::::::::::::::::  :::::::::::::
SEQ ID NO:2   VIGFIGSVFSPWYIRSGRKEPQNICCLNVATYGPGGHFTNETTILGRAALHQSPDTLTVG
                  70        80        90       100       110       120
SEQ ID NO:4   PSRIETHWTGTQLIVEVNEISSPPLVSPVKGRIVLTPTGITDVEVTLKDDGSHIWRPFAP
              ::::::::::::::::::::::::::::::::::::::::::::::::::::::::::::
SEQ ID NO:2   PSRIETHWTGTQLIVEVNEISSPPLVSPVKGRIVLTPTGITDVEVTLKDDGSHIWRPFAP
                 130       140       150       160       170       180
SEQ ID NO:4   TARIEVDLTQGHRWIGHGYFDANFGTAALEADFRPWTWGRYPVADGAACFYDATRHDCSR
              ::::::::::::::::::::::::::::::::::::::::::::::::::::::::::::
SEQ ID NO:2   TARIEVDLTQGHRWIGHGYFDANFGTAALEADFRPWTWGRYPVADGAACFYDATRHDCSR
                 190       200       210       220       230       240
SEQ ID NO:4   LELGLHVAALGRAHLIQPPPEAHFARSRWLVERHTPADPGTRPRQVMETSMETLDAPFYR
              ::::::::::::::::::::::::::::::::::::::::::::::::::::::::::::
SEQ ID NO:2   LELGLHVAALGRAHLIQPPPEAHFARSRWLVERHTPADPGTRPRQVMETSMETLDAPFYS
                 250       260       270       280       290
SEQ ID NO:4   HAMETVETTVFGQKTVGVHEALDLRRFISPLLMETPMETLAVRNPHHPGWSFS
              ::::::::::::::::::::::::::::::::::::::::::::::::::::
SEQ ID NO:2   HAMETVETTVFGQKTVGVHEALDLRRFISPLLMETPMETLAVRNPHHPGWSFS
```

Lycopene standard

Rs-M

Rs-M/A

Rs-E

Rs-E/A

Rs-A

Lycopene

ζ-carotene

Neurosporene

Spheroidenone

Methoxyneurosporene

LYCOGEN EXTRACT, COMPOSITION THEREOF AND METHOD FOR THE TREATMENT USING THE SAME

FIELD OF THE INVENTION

The present invention relates to a lycogen extract, a composition comprising the lycogen extract, and a method for the treatment using the same.

BACKGROUND OF THE INVENTION

Lycopene, with molecular formula of $C_{40}H_{56}$, presents in plasma and other human tissue. The plasma level of lycopene is 2.5 times higher than β-carotene and 7.5 times higher than α-carotene, which can prove the importance of lycopene in human defense system.

Recent studies have shown an anti-oxidative role of lycopene in human body. When compared with β-carotene and vitamin E, lycopene may be the most carotenoid quencher of singlet oxygen, being 100 times more efficient in test tube studies of singlet-oxygen quenching action than vitamin E. Still other epidemiological studies point out that lycopene can significantly enhance resistance to LDL oxidation and therefore prevent human suffering from arteriosclerosis. These suggest that lycopene is helpful in prevention of cardiovascular disease such as myocardial infarction and cardiopathy.

Since lycopene is a powerful antioxidant, it is useful to anticancer and fighting against cardiopathy. However, human body cannot synthesize lycopene which have to be uptake from the diet. In addition, an inverse correlation has been shown between the capability of anti-free radical system and increase in age of human body. Appropriate supplement of lycopene therefore can reduce occurrence of disease and enhance vigor.

Fruits and vegetables that are high in lycopene include those in red and orange color such as tomato, grapefruit, red pepper, watermelon, guava, papaya, almond and products thereof. The fruit contains most lycopene is tomato, and the more reddish the tomato is, the more lycopene it contains. However, lycopene is mainly located inside the cell wall of the tomato, the protein tissue and the fiber tissue. It is therefore hard to be absorbed by human body. According to above reasons, even eat fresh tomato directly, it is still not easy for human body to take lycopene in.

It is general to making commercial lycopene food products by utilizing the liposolubility feature of lycopene. These food products are used to increase lycopene absorption of human body and provide disease resistance. There are even many related patent about this subject matter.

Furthermore, no matter lycopene and β-carotene are reported to be able to protect human lymphocytes from be damaged by free radical such as $NO_2$, the most common toxin in air pollution and smoking. The $NO_2$ resistant effect of lycopene is at least two times of that of β-carotene. A lycopene supplement is therefore absolutely helpful to air pollution or secondhand smoke issue.

Considering the above-mentioned benefits of lycopene for human body and limited amount and speed of extraction, the way to extract a great quantity of lycopene with high speed and make it totally absorbed by human body is actually a great issue for biotech entrepreneur. There are many patents, such as U.S. Pat. Nos. 5,530,189, 5,429,939 and 5,304,478, disclose needed gene sequences for gene recombination to synthesize lycopene. Transferring these sequences into bacteria will enable them to generate lycopene with high purity. However, there is still no patent about mutated bacteria capable of lycogen.

BRIEF DESCRIPTION OF THE DRAWINGS

The invention can be more fully understood by reading the subsequent detailed descriptions and examples with references made to the accompanying drawing, wherein:

FIG. 3 shows CrtC enzyme DNA sequence comparison between mutant (SEQ ID NO: 1) and wildtype (SEQ ID NO: 3) photosynthetic bacteria according to one embodiment of the present invention.

FIG. 4 shows CrtC enzyme amino acid sequence comparison between mutant (SEQ ID NO: 2) and wildtype (SEQ ID NO: 4) photosynthetic bacteria according to one embodiment of the present invention.

SUMMARY OF THE INVENTION

Figure 1:
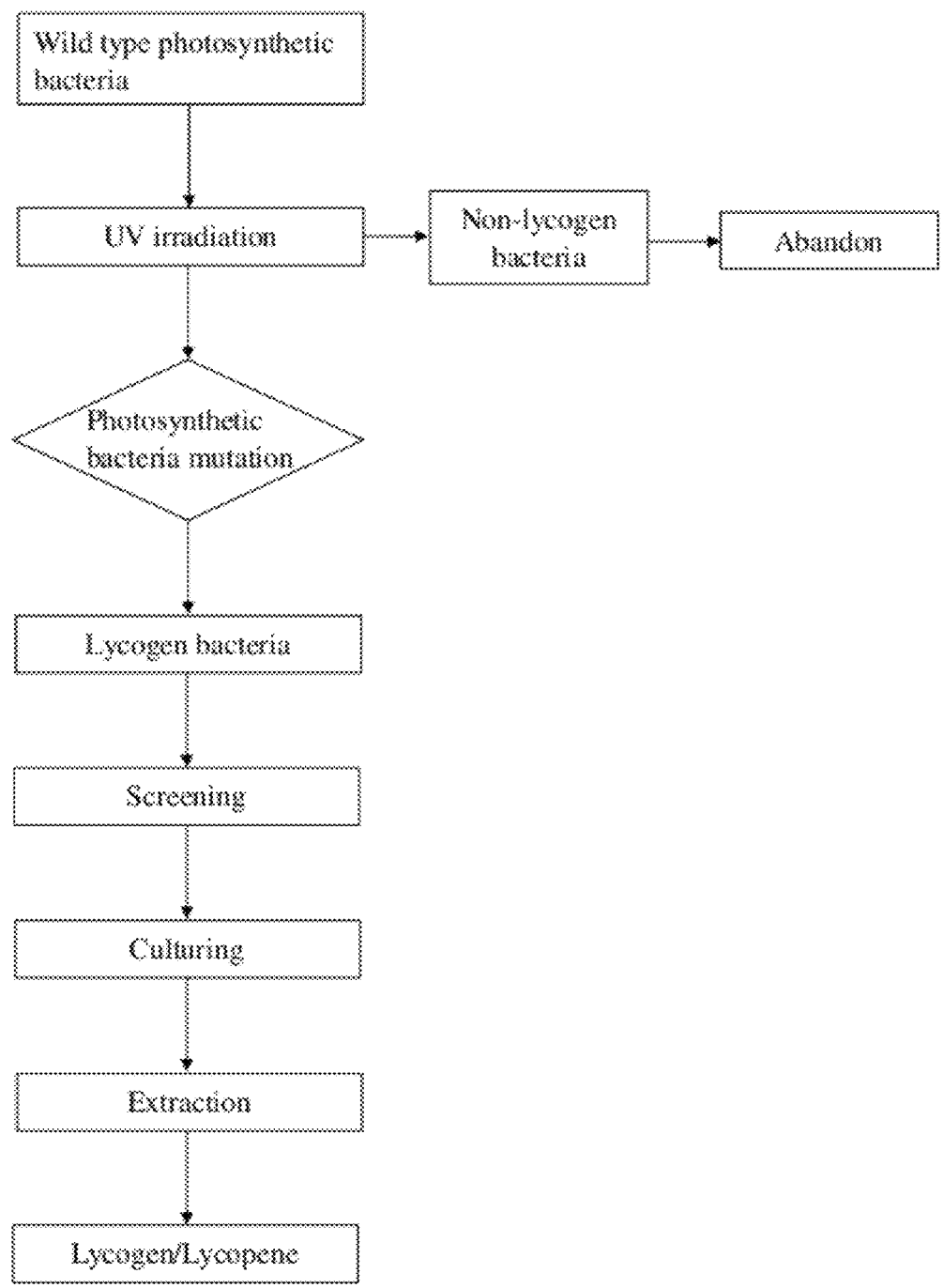
FIG. 1 shows the flowchart for producing mutant photosynthetic bacteria according to one embodiment of the present invention.

The present invention relates to a lycogen extract comprising active ingredient of ζ-carotene, neurosporene, spheroidenone and/or methoxyneurosporene. The present invention also relates to a composition comprising the lycogen extract, which comprises active ingredient of ζ-carotene, neurosporene, spheroidenone and/or methoxyneurosporene, and food scientific or pharmaceutical acceptable carrier. The present invention further relates to a method for the treatment of disease in need of the lycogen extract, which comprises active ingredient of ζ-carotene, neurosporene, spheroidenone and/or methoxyneurosporene, which comprises administering to a patient in need thereof a therapeutically effective amount of lycogen extract of the present invention.

DETAILED DESCRIPTION OF THE INVENTION

Before the present extract, composition and treatment methodology are described, it is to be understood that the terminology used herein is for purposes of describing particular embodiments only, and is not intended to be limiting, since the scope of the present invention will be limited only in the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the particular methods and materials are now described. All publications mentioned herein are incorporated herein by reference.

As used hereinafter, the term "lycogen" refers to a bacterial substance extracted from mutant photosynthetic bacteria, which had been deposited in Food Industry Research and Development Institute (Hsinchu, Taiwan), with deposit number of BCRC910406. Also, the mutant photosynthetic bacteria had been deposited in DSMZ (Deutsche Sammlung von Mikroorganismen und Zellkulturen GmbH) which belongs to International Depository Authority (IDA) under the Budapest Treaty is located at Inhoffenstraβe 7B, 38124 Braunschweig, Germany, with deposit number of DSM 25056. The deposit of DSM 25056 was received on Aug. 1, 2011 and the viability of the deposited microorganism was tested on Aug. 1, 2011 and was tested to be viable. According to one embodiment of the present invention, the photosynthetic bacteria are *Rhodobacter sphaeroides*, which is mutated from wild type primary photosynthetic bacteria by utilizing UV irradiation. According to another embodiment of the present invention, the lycogen is extracted with organic solvent such as, but not limit to, methanol, ethanol, acetone, n-butanol, n-hexane, dicholoromethane or ethyl acetate. According to HPLC analysis result (FIG. 5), the retention time of lycogen, which is between 21.7 to 24.19 min, is different from that of lycopene.

As used hereinafter, the term "organic solvent" refers to methanol, ethanol, acetone, n-butanol, n-hexane, dicholoromethane, ethyl acetate or any other solvent of organic compound that one skilled in the art will recognize that is suitable for utilizing in an extraction process.

As used hereinafter, the term "anti-inflammation" or "anti-inflammatory effect" refers to the property of a substance or treatment that reduces inflammation. According to one embodiment of the present invention, the "anti-inflammation" or "anti-inflammatory effect" by inhibiting iNOS or/and COX-II protein expression or NO release.

As used hereinafter, the term "skin lightening" refers to the practice of using chemical substances in an attempt to lighten skin tone or provide an even skin complexion by lessening the cellular concentration of melanin. It is also known as "skin whitening" or "skin bleaching".

As used hereinafter, the term "anti-oxidation" or "anti-oxidative effect" refers to refers to the property of a substance or treatment capable of removing free radical intermediates, and inhibit other oxidation reactions. According to one embodiment of the present invention, the "anti-oxidation" or "anti-oxidative effect" is achieved by inducing of activities anti-oxidative enzymes. In one embodiment of the present invention, the anti-oxidative enzyme is GPX (glutathione peroxidase).

As used hereinafter, the term "lycopene standard" or "standard" refers to lycopene extracted from tomato (commercially purchased from Sigma-Aldrich).

As used hereinafter, the term "patient" refers to a person under or requires health or medical care and/or treatment. Wherein, the person may be waiting for this care or may be receiving it or may have already received it.

As used herein, the term "a" or "an" are employed to describe elements and components of the invention. This is done merely for convenience and to give a general sense of the invention. This description should be read to include one or at least one and the singular also includes the plural unless it is obvious that it is meant otherwise.

As used herein, the term "or" are employed to describe "and/or".

Accordingly, the present invention provides a lycogen extract comprising active ingredient of ζ-carotene, neurosporene, spheroidenone and/or methoxyneurosporene.

In one embodiment, the active ingredient is extracted from mutant photosynthetic bacteria. In another embodiment, the mutant photosynthetic bacteria are *Rhodobacter sphaeroides* with deposit number of BCRC910406. In still another embodiment, the mutant photosynthetic bacteria comprises DNA sequence as shown in SEQ ID NO:1 for CrtC enzyme (hydroxyneurosporene dehydrogenase), where the wild type photosynthetic bacteria comprises DNA sequence as shown in SEQ ID NO:3 for said enzyme. In another embodiment, the mutant photosynthetic bacteria comprises amino acid sequence as shown in SEQ ID NO:2 for CrtC enzyme, where the wild type photosynthetic bacteria comprises amino acid sequence as shown in SEQ ID NO:4 for said enzyme.

In one embodiment, the ζ-carotene is more than 10% by weight of the lycogen extract. In another embodiment, the neurosporene is more than 10% by weight of the lycogen extract. In still another embodiment, the spheroidenone is more than 30% by weight of the lycogen extract. In another embodiment, the methoxyneurosporene is more than 30% by weight of the lycogen extract. Among the above embodiments, the total amount of ζ-carotene, neurosporene, spheroidenone and methoxyneurosporene is no more than 100% by weight of the lycogen extract.

In one embodiment, the ratio of the spheroidenone and methoxyneurosporene within the lycogen extract is about 1:1.

In one embodiment, the ζ-carotene is about 10-20% by weight of the lycogen extract. In another embodiment, the neurosporene is about 10-20% by weight of the lycogen extract. In still another embodiment, the spheroidenone is about 30-45% by weight of the lycogen extract. In another embodiment, the methoxyneurosporene is about 30-45% by weight of the lycogen extract. Among the above embodiments, the total amount of ζ-carotene, neurosporene, spheroidenone and methoxyneurosporene is no more than 100% by weight of the lycogen extract.

In one embodiment, the ζ-carotene is about 10.58% by weight of the lycogen extract. In another embodiment, the neurosporene is about 13.47% by weight of the lycogen extract. In still another embodiment, the spheroidenone is about 37.37% by weight of the lycogen extract. In another embodiment, the methoxyneurosporene is about 38.58% by weight of the lycogen extract. Among the above embodiments, the total amount of ζ-carotene, neurosporene, spheroidenone and methoxyneurosporene is no more than 100% by weight of the lycogen extract.

The present invention also provides a composition comprising the lycogen extract of the present invention and food scientific or pharmaceutical acceptable carrier.

In one embodiment, the composition can be used to anti-inflammation, anti-oxidation, skin lightening, inhibit collagen degradation or increase collagen production. In another embodiment, the composition can be used as food supplement, animal feed, human food product or pharmaceutical or cosmetic composition.

The present invention further provides a method for the treatment of disease in need of the lycogen extract of the present invention which comprises administering to a patient in need thereof a therapeutically effective amount of lycogen extract of the present invention.

The next examples provide some exemplary embodiments of the present invention as follows:

EXAMPLES

The examples below are non-limiting and are merely representative of various aspects and features of the present invention.

Please refer to the flowchart of FIG. 1 for producing mutant photosynthetic bacteria according to one embodiment of the present invention. The present invention provides a microorganism which produces lycopene and lycogen. The method to generate said microorganism comprising irradiating the wild type primary photosynthetic bacteria with UV light for 5, 10, 20, 30 or 40 seconds to make it transformed. After the photosynthetic bacteria transformed into mutated photosynthetic bacteria which is rich in lycogen (named lycogen bacteria), they are screened out, cultured and extracted with organic solvent to obtain lycogen.

Figure 2:
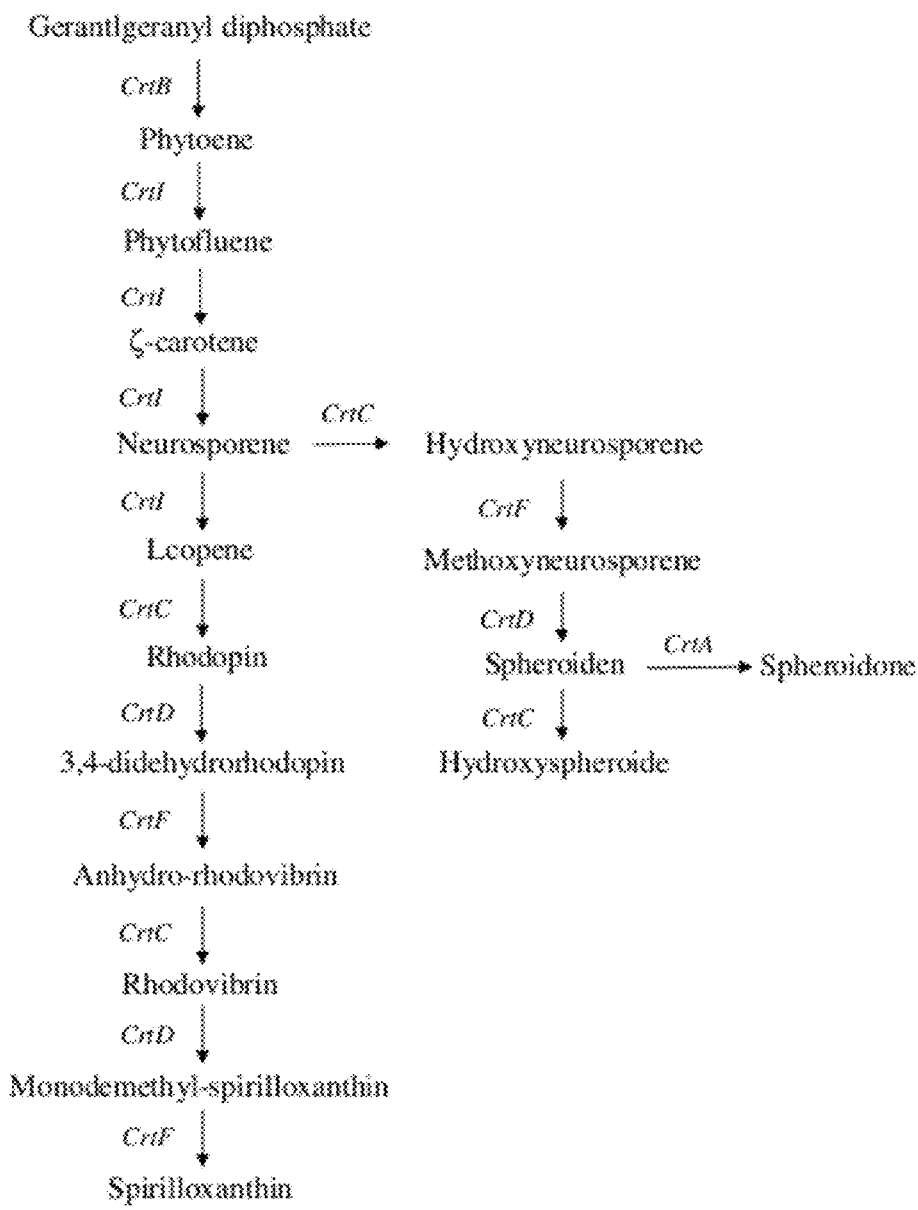
FIG. 2 shows the metabolic pathway of photosynthetic bacteria starting from geranylgeranyl diaphosphate.

Please refer to the metabolic mechanism of photosynthetic bacteria as shown in FIG. 2 according to one embodiment of the present invention. The metabolism starts with geranylgeranyl diphosphate, which is converted into phytoene by enzyme CrtB. The phytoene is then sequentially converted into phytofluene, ζ-carotene, neurosporene and lycopene by enzyme CrtI. When proceeding with the metabolic process, the lycopene is converted into rhodopin by enzyme CrtC and 3,4-didehydrorhodopin by enzyme CrtD. The 3,4-didehydrorhodopin is then converted into anhydro-rhodovibrin by enzyme CrtF. The anhydro-rhodovibrin is then sequentially converted into rhodovibrin, monodemethyl-spirilloxanthin and finally spirilloxanthin by enzyme CrtC, CrtD and CrtF respectively. In above-mentioned metabolic process, the neurosporene can also be converted into hydroxyneurosporene by enzyme CrtC, which then sequentially converted into methoxyneurosporene and spheroidene by CrtF and CrtD respectively. In addition, the above spheroidene can also be converted into hydroxyspheroidene by enzyme CrtC or into spheroidnone by enzyme CrtA.

After receiving of UV irradiation, the color of the primary photosynthetic bacteria of the present invention changed. When the primary photosynthetic bacteria mutated into lycogen bacteria with bright red color, the bacterial liquid is isolated and cultured. The DNA sequence of the cultured lycogen bacteria is shown as SEQ ID NO: 1. When compared with the wild type primary photosynthetic bacteria, the mutated lycogen bacteria possess mutation at the 76, 88, 147, 214, 274, 282, 310, 496, 694, 707, 708 and 715 nucleotides (as shown in FIG. 3). Therefore, it can be sure that the mutated bacteria with mutation at the 76, 88, 147, 214, 274, 282, 310, 496, 694, 707, 708 and 715 nucleotides are lycogen bacteria containing lycogen. The amino acid sequence of the lycogen bacteria is shown as SEQ ID NO:2. When compared with the wild type primary photosynthetic bacteria, the mutated lycogen bacteria possess mutation at the 45, 46, 47, 190 and 239 amino acids (as shown in FIG. 4). Therefore, it can be sure that the mutated bacteria with mutation at the 45, 46, 47, 190 and 239 amino acids are lycogen bacteria containing lycogen. These above-mentioned mutations result in impaired enzyme CrtC (refer to FIG. 1). These lycogen bacteria are then screened, cultured and extracted with organic solvent to obtain the lycogen.

In the present invention, the mutated bacterial strain is produced by utilizing physical UV irradiation on wild type primary photosynthetic bacteria for various time lengths. The lycogen bacteria with bright red color are screened, cultured and extracted with organic solvent to obtain the lycogen. Therefore, the great amount of lycogen can be obtained without extraction of tomato.

Example 1

Extraction and Isolation of Lycogen

1. Methanol and Acetone Extracts

The mutant photosynthetic bacteria of the present were vortexed in methanol and subjected to 8000 rpm centrifugation for 10 min. The supernatant was collected and filtered. The above-mentioned extraction steps were repeated for three times and those filtrates were combined. The combined filtrate was concentrated in reduced pressure to obtain the methanol lycogen extract (Rs-M). The bacterial residue of methanol extraction was then extracted with acetone followed above steps. The filtrate was concentrated in reduced pressure to obtain the acetone lycogen extract (Rs-M/A).

2. Ethanol and Acetone Extracts

As the steps described above, except that methanol was replaced with ethanol. Therefore, the ethanol lycogen extract (Rs-E) and the acetone lycogen extract (Rs-E/A) were obtained.

3. Acetone Extract

As the steps described above, except that only acetone was used in this part. Therefore, the acetone lycogen extract (Rs-A) was obtained.

4. Isolation of Extracts

The extracts were added with distilled water, suspended and extracted with n-hexane for three times. The combined extracts were concentrated under reduced pressure to dry to obtain the n-hexane layer (Fr, Rs-H). The water layer was then sequentially increased the polarity and extracted with dichloromethane, ethyl acetate and water-saturated n-butanol to obtain the dichloromethane layer (Fr, Rs-C), ethyl acetate layer (Fr, Rs-E) and n-butanol layer (Fr, Rs-B), respectively. The remaining substance was the water layer (Fr, Rs-W).

Example 2

High-Performance Liquid Chromatography (HPLC) Analysis

HPLC was employed to analyze the bacterial pigment content. The powder of bacterial lycogen extract was dissolved in DMSO and protected from light. HPLC condition is as follows: C18 column, wave length 470 nm, mobile phase of methanol/isopropanol (95/5, v/v), flow rate of 1 ml/cm, and retention time (lycopene standard) of 50±2 min.

Figure 5A:
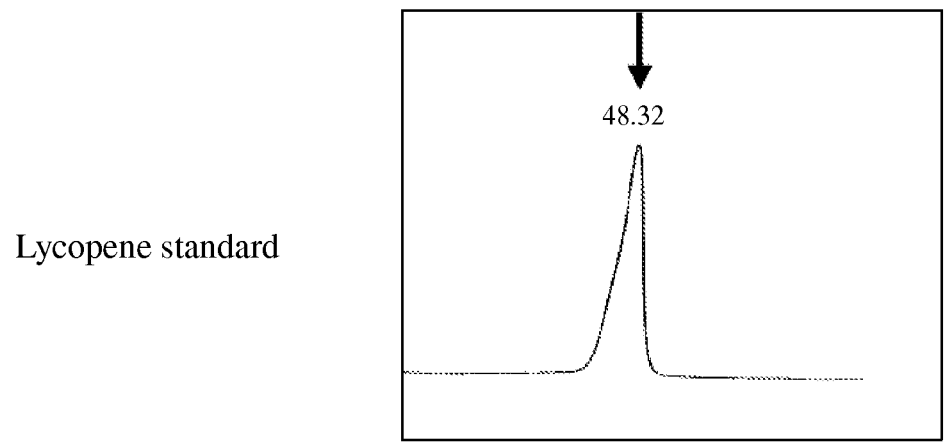
FIG. 5 shows HPLC analysis diagram; (A) to (F) are the results of lycogen extracted by different organic solvent from photosynthetic bacteria according to one embodiment of the present invention; (G) is the result of lycopene standard; (H) is the result of ethanol acetone lycogen extract according to one embodiment of the present invention.
Figure 5B:
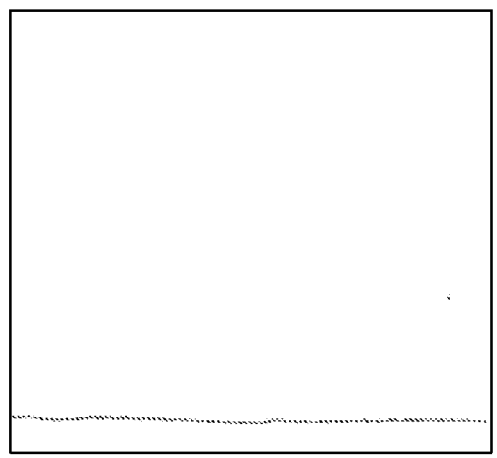
Figure 5C:
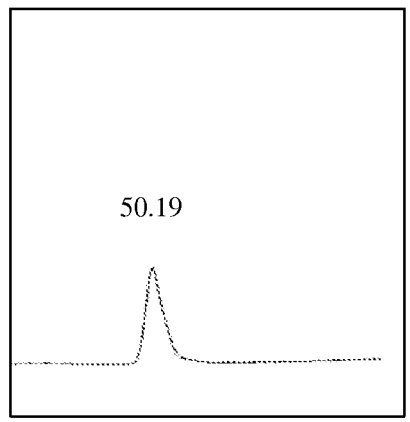
Figure 5D:
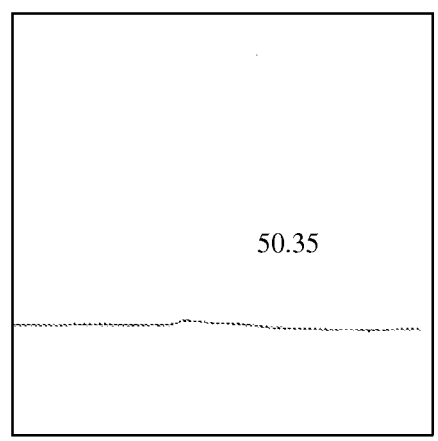
Figure 5:
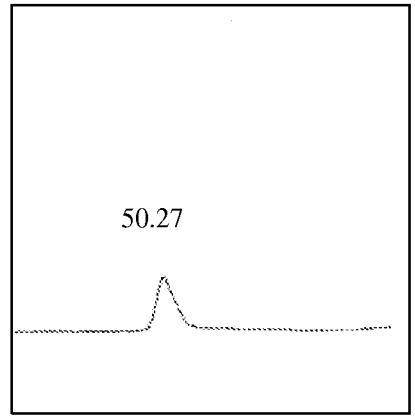
Figure 5:
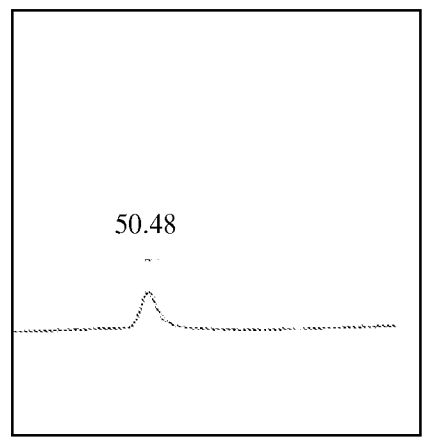
Figure 5:
Figure 5:
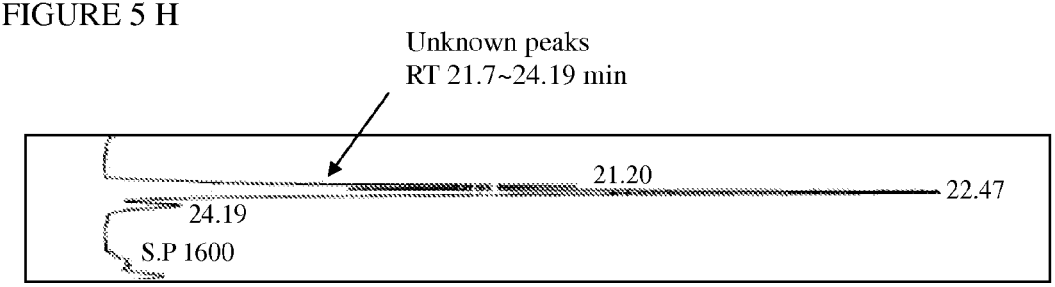

The methanol extract (Rs-M) was in green color, the ethanol extract (Rs-E) was in dark brown color and the acetone extract (Rs-A) was in dark red color. Compared with the lycopene standard, Rs-A contained the greatest amount of lycopene (RT=50 min), the Rs-E contained trace amount of lycopene, and the Rs-M contained none. These suggest that there were still lycopene in the methanol and ethanol extracted residues. The methanol and ethanol extracted residues were therefore extracted again with acetone respectively. The resulted acetone extract of methanol residue (Rs-M/A) and acetone extract of ethanol residue (Rs-E/A) were both in red color. Rs-M/A and Rs-E/A were also subjected to HPLC analysis. The test results are shown in FIGS. 5 (A) to (F) where the arrowhead points to the absorption peak of lycopene.

The ethanol acetone extract (Rs-E/A) of bacteria was dissolved in DMSO and analyzed with HPLC. The retention time of the Rs-E/A was compared with that of the lycopene standard (L-9879, Sigma) (FIG. 5(G)). In the HPLC chromatogram of the bacterial extract, the peak shown at the same retention time with the lycopene standard (50 min) was low, where the highest peak was shown at retention time of about 21 min (about 21.7~24.19 min, which was named as unknown peak) (FIG. 5(H)). This result suggested that the main ingredient of the bacterial extraction that absorbed the light of 470 nm was the substance shown at 21 min. It was possible that this substance was an intermediate metabolite of lycopene synthesis. Therefore, the material was named as "lycogen". The area of the lycopene peaks was only 3.3% of that of the lycogen peak.

Example 3

Test of Anti-Inflammation

1. Cell Culture

The mouse RAW 264.7 macrophages were cultured in DMEM containing 10% fetal bovine serum and antibiotics (100 U/ml penicillin and 100 μg/ml streptomycin). The cells were incubated in 5% $CO_2$ incubator under 37° C.

2. iNOS Expression

Figure 6A:
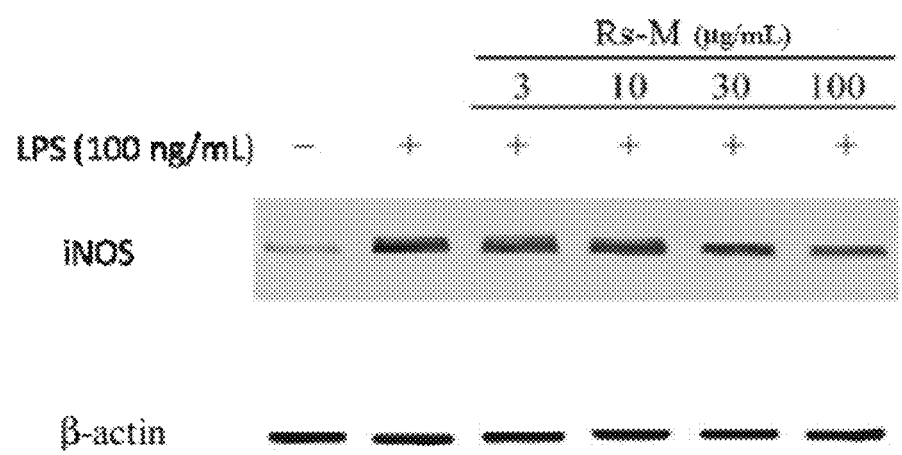
FIG. 6 shows Western results demonstrating iNOS and COX-II protein expression of RAW 264.7 cells after LPS stimulation and treatment of methanol lycogen extract according to one embodiment of the present invention.
Figure 6B:
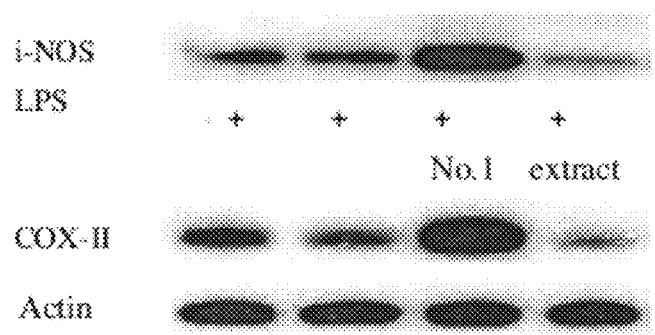

According to report of Wu (2008), the anti-inflammation substance of modified *Rhodobacter sphaeroide* can inhibit LPS-induced NO production of RAW 264.7 macrophages. NO release of RAW 264.7 macrophages was induced by LPS, and the iNOS and COX-II protein expression were observed (FIG. 6). Under the condition with LPS stimulation, iNOS and COX-II protein expression level demonstrated inverse proportion against the concentration of bacterial extract (FIG. 6). The quantitative result of iNOS and COX-II protein expression of FIG. 6 (B) was shown in table 1. These results suggested that both the Rs-M and the Rs-E exhibited anti-inflammatory effect.

TABLE 1

|  | iNOS | COX-II | actin |
| --- | --- | --- | --- |
| LPS | 965.3216 | 1590.5825 | 2698.9823 |
| LPS | 692.8529 | 677.965 | 2727.258 |
| No.1 | 3533.338 | 4411.8988 | 2765.6662 |
| extract | 121.9883 | 164.9038 | 2544.9091 |

3. Inhibition of NO Release

The RAW 264.7 macrophages were stimulated with LPS and treated with 100 μg/ml of organic solvent extracts (Rs-M, Rs-M/A, Rs-E, Rs-E/A, Rs-A) for 24 hr. The NO release was than measured. These results showed that the Rs-M demonstrated the most significant inhibitory effect on NO release. The inhibitory effect of each extract was Rs-M>Rs-A>Rs-E, where Rs-M/A and RsE/A were without obvious anti-inflammatory activity. The anti-inflammatory activity of Rs-M, which was without lycopene presence, was higher than other four kinds of extracts. Therefore, the anti-inflammatory effect of the modified *R. sphaeroide* was suggested to be irrelevant with lycopene.

Figure 7:
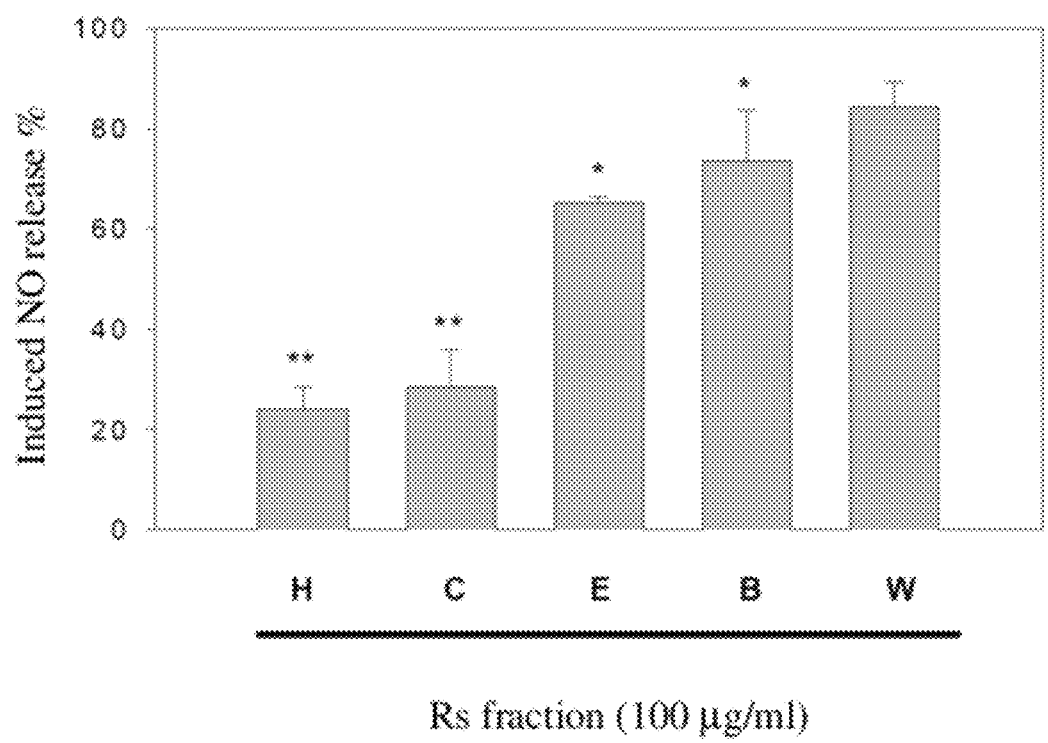
FIG. 7 shows the test results of NO releasing, which are affected by different organic solvent lycogen extract according to one embodiment of the present invention. RAW 264.7 macrophages are stimulated by LPS, treated with different organic solvent extract of mutant photosynthetic bacteria of the present invention and measured of the NO releasing.

Following, the extracts obtained by using of n-hexane (H), diachloromethane (C), ethyl acetate (E), n-butanol (B) and water (W) were also tested for their inhibitory effect on NO release. As shown in FIG. 7, the n-hexane (H) extract and diachloromethane (C) extract demonstrated the most significant inhibitory effect.

The lycogen, which was extracted from the mutant photosynthetic bacteria of the present invention, was used in the following examples. The extract was obtained by utilizing ethanol acetone extraction. The extraction steps were the same as those described above.

Example 4

Analysis of Anti-Oxidative Ability

1. Grouping and Feeding of the Animal

The 3 to 4 weeks-old Wistar rats were used. The rats were adapted for 3 to 5 days before the analysis and grouped into control group (group C, fed with a control diet) and test group (group Lyc, fed with a lycogen containing diet) according to their body weight. To avoid oxidation of lycogen causing by light irradiation and long term air exposure, the lycogen powder was mixed with corn starch and provided once a day at the fixed time point (20 mg/kg). After 3 weeks of breeding, the group C was further divided into 2 subgroups (group C−Fe and group C+Fe). One of the control subgroups and the group Lyc were intraperitoneal injected with Fe-NTA (10 mg/kg per day), which were denoted as group C+Fe and group Lyc+Fe respectively. 3 hr later, these rats were sacrificed with $CO_2$ inhalation. The blood samples were collected from vena cava inferior and processed to obtain the serum. Other tissues were also harvested and stored in freezer for analysis in the future.

2. Detection of TBARS (Thiobarbituric Acid-Reactive Substances)

TBARS is a common index of tissue lipid peroxidation, which is induced by Fe-NTA injection. The anti-oxidative ability of bacterial lycogen extract was observed under the above condition, and the test results were shown in table 2. Regarding the liver and the kidney tissues, TBARS values of both groups C+Fe and Lyc+Fe were higher than that of the group C−Fe. However, in the spleen and prostate tissues, TBARS value of group C+Fe was significantly higher than that of group Lyc+Fe, when the TBARS value of group C−Fe was the lowest one. The test results showed that the bacterial lycogen extract can decrease the peroxides of spleen and prostate tissues, which meant protection for these tissues.

TABLE 2

The TBARS concentration in various tissues of rat fed a control diet or lycopene containing diet

| nmol/g tissue | Control | | Lyc (lycogen) |
|---|---|---|---|
| | − Fe | + Fe | + Fe |
| Liver | $13.2 \pm 3.4^b$ | $156.0 \pm 25.8^a$ | $153.1 \pm 43.6^a$ |
| Kidney | $32.6 \pm 7.3^b$ | $146.4 \pm 13.8^a$ | $150.7 \pm 6.0^a$ |
| Spleen | $12.7 \pm 4.4^b$ | $21.4 \pm 10.3^a$ | $12.2 \pm 3.1^b$ |
| Prostate | $16.59 \pm 4.8^b$ | $81.0 \pm 25.0^a$ | $42.0 \pm 14.8^b$ |

1. Each value is the mean ± SD (n = 6).
2. Values not sharing common superscript are significantly different from one another among the three groups by one-way ANOVA and Ducan's multiple range test (p < 0.05).

3. Measurement of GSH (Glutathione)

1 ml tissue homogenate was added with 5% TCA (tricholroacetic acid) solution. The resulted TCA supernatant was reacted with DTNB (5,5'-dithiobis-(2-nitrobenzoic acid)) and measured the absorbance under 412 nm (Sedlak and Lindsay, 1968). The absorbance curve was compared with the standard curve.

GSH content of Fe-NTA treated liver, kidney and spleen were lower than those of non-treated tissues. Application of bacterial lycogen extract significantly increased GSH content of liver (as shown in table 3). However, GSH contents of kidney and spleen were not significantly changed by lycogen containing diet treatment. GSH contents of prostate were similar among these three groups. This suggested that increase of tissue TBARS with Fe injection may not caused by GSH consumption.

TABLE 3

The concentration of reduced glutathione (GSH) in various tissues of rats fed with control diet or lycogen containing diet.

| nmol/g tissue | Control | | Lyc (Lycogen) |
|---|---|---|---|
| | − Fe | + Fe | + Fe |
| Liver | $3.384 \pm 0.895^a$ | $0.656 \pm 0.157^c$ | $1.448 \pm 0.444^b$ |
| Kidney | $3.100 \pm 0.759^a$ | $1.597 \pm 0.801^b$ | $11.921 \pm 0.224^b$ |
| Spleen | $1.360 \pm 0.262^a$ | $0.631 \pm 0.198^a$ | $0.997 \pm 0.332^{ab}$ |
| Prostate | $0.335 \pm 0.048^a$ | $0.334 \pm 0.068^a$ | $0.337 \pm 0.096^a$ |

1. Each value is the mean ± SD (n = 6).
2. Values not sharing common superscript are significantly different from one another among the three groups by one-way ANOVA and Ducan's multiple range test (p < 0.05).

4. Measurement of GPX (Glutathione Peroxidase) Activity

Enzyme activity was measured in cell supernatant derived from tissue centrifugation. The reaction of the measurement was as follows: $H_2O_2 + 2GSH \rightarrow GSSG + 2H_2O$, Since GSSG could be reduced by NADPH through glutathione reductase reaction, i.e. $GSSG + NADPH + H^+ \rightarrow 2GSH + NADP^+$, GPX activity could be calculated according to absorbance decrease level of NADPH under 340 nm. 1 activity unit of GPX reduced 1 μM NADPH per minute (Pagli and Valentine, 1967).

Regarding enzyme activities of SOD and catalase in liver, there was no significant difference between the 3 groups (as shown in table 4). After Fe-NTA and lycogen extract treatment, GPX activity was significantly increased. In liver of rat, GPX activity was increased and the TBARS value was reduced through feeding the animal with tomato powder (Moreira et al., 2005). This suggested that bacterial lycogen extract was characterized with the ability to induce liver GPX enzyme activity. Bacterial lycogen extract could also protect liver from peroxidation. Therefore, it has similar effect with the tomato lycopene.

TABLE 4

The activities of SOD, GPX and catalase in liver and kidney of rats fed a control diet or lycogen containing diet.

| | Control | | Lyc (Lycogen) |
|---|---|---|---|
| | − Fe | + Fe | + Fe |
| SOD (U/mg prot.) | $8.954 \pm 1.958$ | $9.337 \pm 4.363$ | $11.737 \pm 2.907$ |
| GPX (U/mg prot.) | $52.4 \pm 12.9^b$ | $47.5 \pm 8.9^b$ | $81.2 \pm 30^a$ |
| Catalase (U/mg prot.) | $1038 \pm 307$ | $1183 \pm 240$ | $1034 \pm 342$ |

1. Each value is the mean ± SD (n = 6).
2. Values not sharing common superscript are significantly different from one another among the three groups by one-way ANOVA and Ducan's multiple range test (p < 0.05).

Example 5

Analysis of Melanin Content

Figure 8:
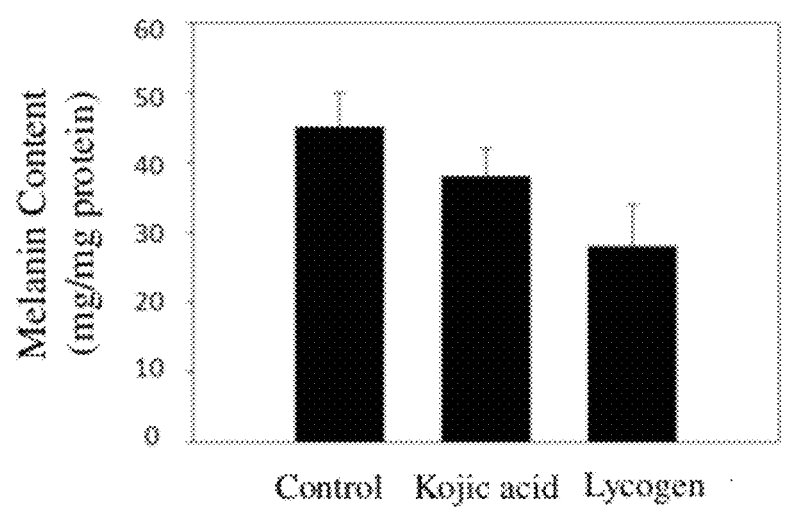
FIG. 8 shows the analysis result for effect of lycogen extract of the present invention upon melanin content. Melanoma cells were treated with lycogen of the present invention for 24 hr and the content of melanin was then measured (mg/mg protein).

Melanoma cells were treated with 3 μM kojic acid or 20 μM lycogen extract of the present invention for 24 hr. The melanin content of cells (mg/mg protein) in each group was measured to study the melanin inhibitory effect of these treatments. According to results shown in FIG. 8, the melanin inhibitory effect of the lycogen extract was better than the commercial kojic acid. That is, the lycogen extract possessed a better skin lightening effect.

Figure 9A:
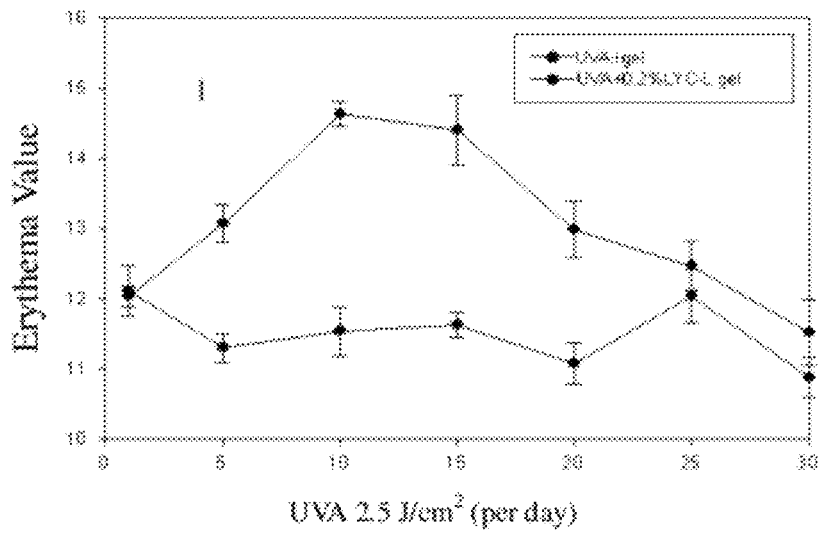
FIG. 9 shows inhibition of erythema value and melanin value in UV irradiated hamsters according to one embodiment of the present invention. The hamsters were irradiated by UV crosslinker box for 30 days with total irradiation amount of 2.5 $J/cm^2$ per day. 0.5 g gel with or without 0.2% lycogen extract of the present invention was applied to the hamsters after irradiation. The erythema value (A) and melanin value (B) were then measured.
Figure 9B:
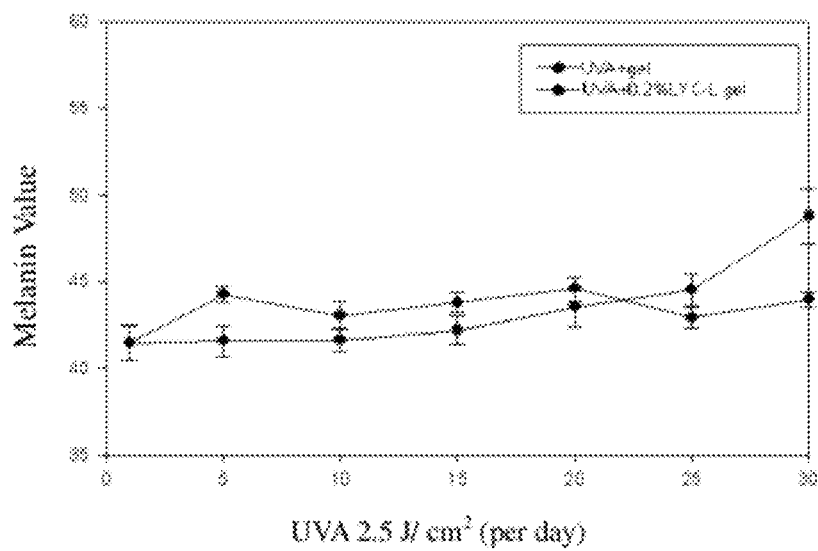

1. Animal Experiment of Erythema and Melanin 6 week-old male Syrian hamsters purchased from National Laboratory Animal Center were used. 12 hamsters were divided into 2 groups, control group and test group, equally. Among 30 days of the experiment process, the hamsters were fed with a control diet. The animals were shaved on the back side and irradiated with UV crosslinker of 2.5 J/cm² per day for 30 days continually. After every time irradiation, gels (0.5 g) containing with or without 0.2% extract of the present invention were applied to skin of the test or control group respectively. 2 hr after the application, DSM II COLORMETER was used to measure skin erythema and melanin values. As shown in FIGS. 9 (A) and (B), skin erythema value was increased significantly after UV treatment and decreased 10 days later. The possible reason could be (1) skin and dermis layer were damaged after receiving UV stimulation; erythema was therefore generated, and the skin keratinization was then started to provide protaction; and (2) the erythema reaction was started under the condition of UV irradiation; the melanin production was then induced (FIG. 9 (B)), and the skin damage from UV was therefore reduced. The skin melanin level showed inverse proportion to the erythema value. These results showed that application of gel containing 0.2% lycogen extract of the present invention could mitigate the erythema reaction. It also could reduce the melanin production in response to UV irradiation.

Example 6

Analysis of Procollagen Content

The Hs68 human fibroblasts were treated with 20 J/cm² of UVA and then with 10, 25 and 50 μM of lycogen extract for 24 hr. The type I procollagen level was analyzed by using Western blotting analysis. As shown in FIG. 9, the lycogen extract of the present invention with concentration higher than 10 μM was able to inhibit the UV-induced collagen degradation.

Figure 10:
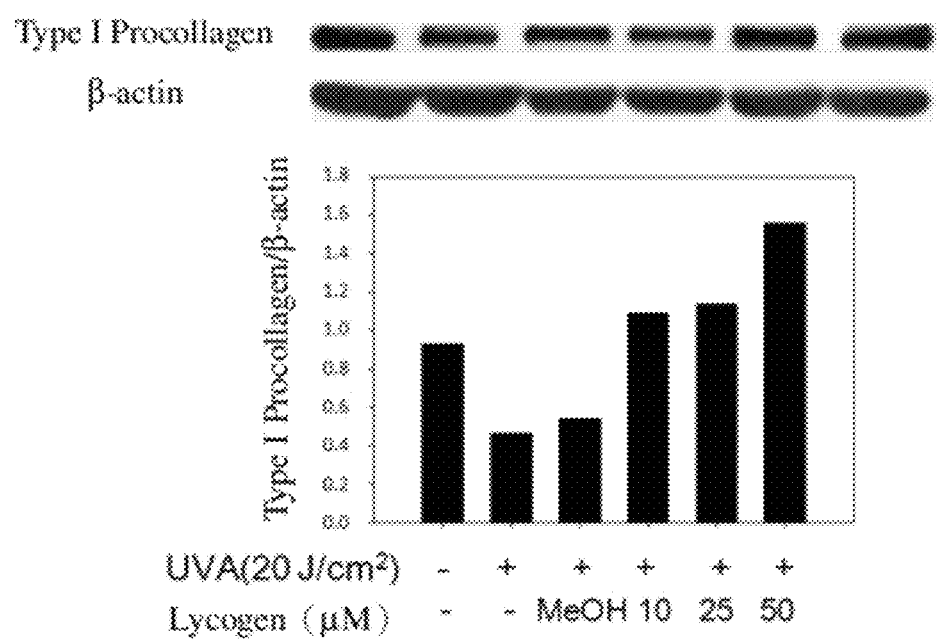
FIG. 10 shows the test results of inhibition of UV-induced collagen degradation according to one embodiment of the present invention. Cells had been or had not been stimulated with UV were treated with 10, 25 and 50 μM lycogen of the present invention. The content of type I collagen was then analyzed by utilizing Western blotting.
Figure 11A:
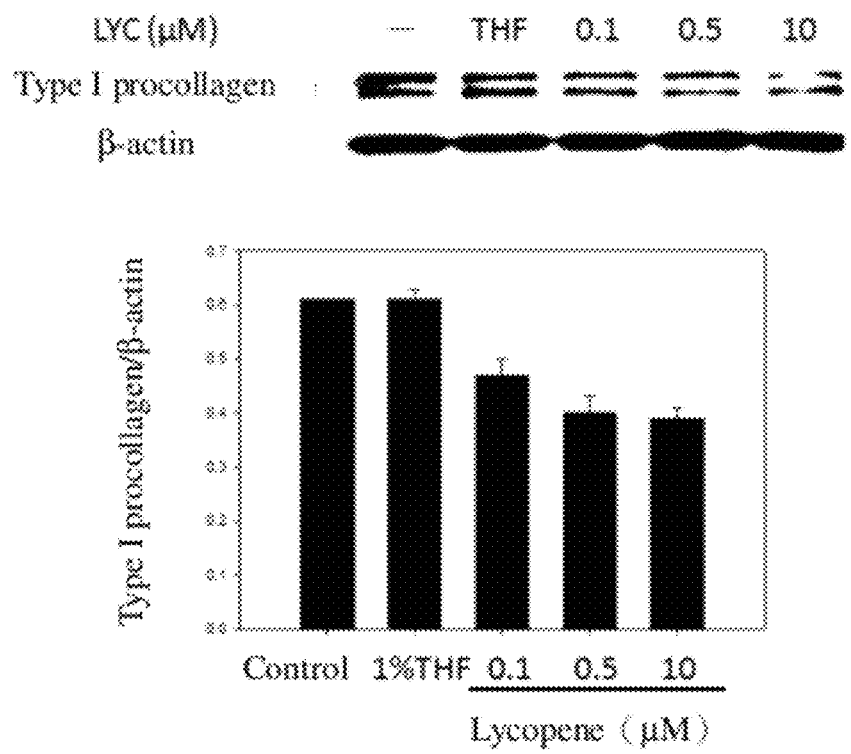
FIG. 11 shows the effect of lycogen extract according to one embodiment of the present invention (A) and lycopene (B) on type I precollagen under condition without UV irradiation.
Figure 11B:
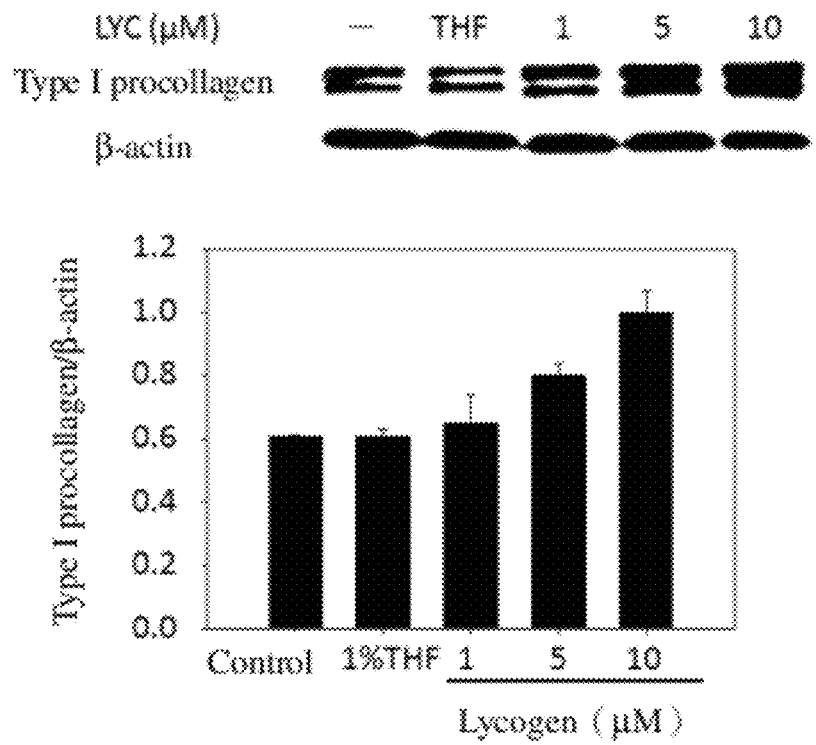
Figure 12A:
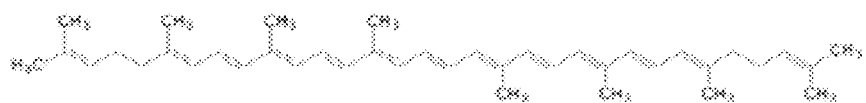
FIG. 12 shows the molecular structures of (A) lycopene; (B) ζ-carotene; (C) neurosporene; (D) spheriodenone and (E) methoxyneurosporene.
Figure 12B:
Figure 12C:
Figure 12D:
Figure 12E:
Figure 13A:
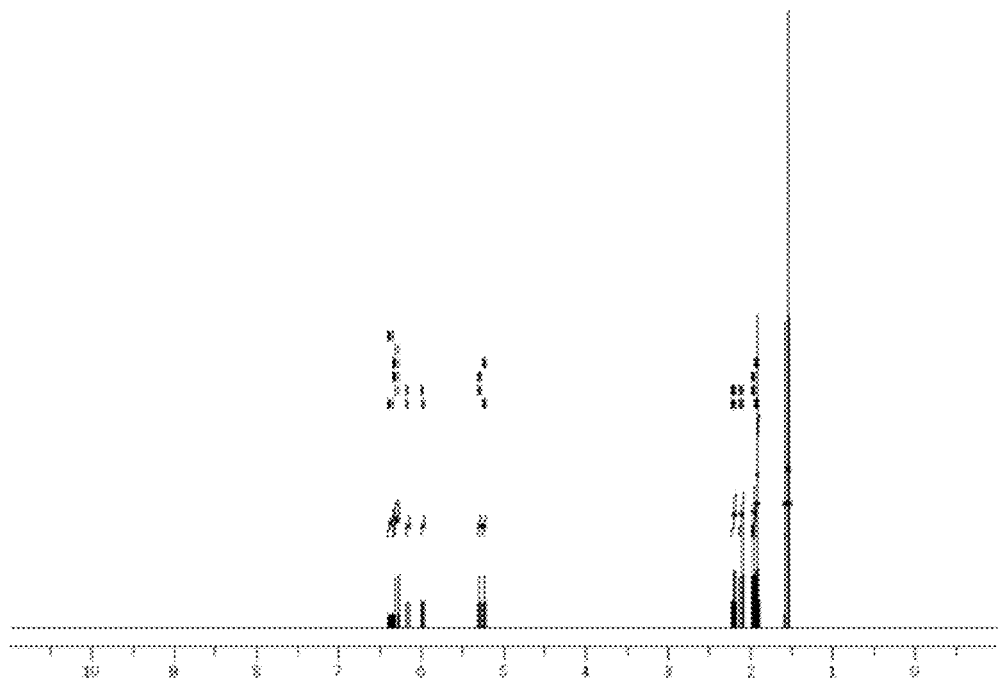
FIG. 13 shows the predicted NMR spectrum of (A) ζ-carotene; (B) neurosporene; (C) spheriodenone and (D) methoxyneurosporene. The marked peaks refer to those can be matched with peaks shown on the COSY NMR spectrum of the lycogen extract.
Figure 13B:
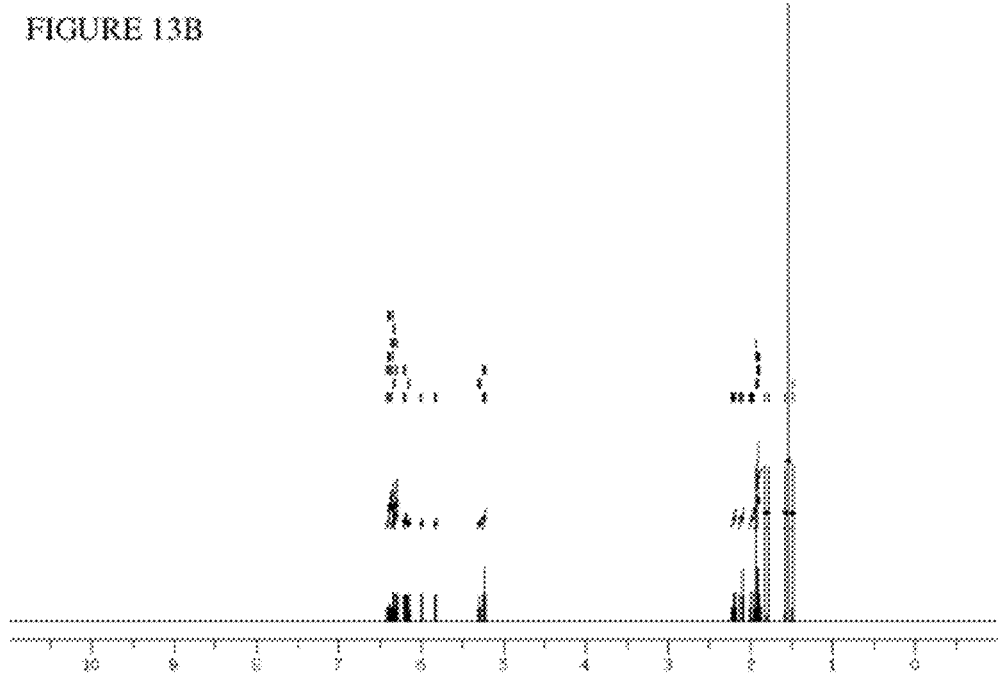
Figure 13C:
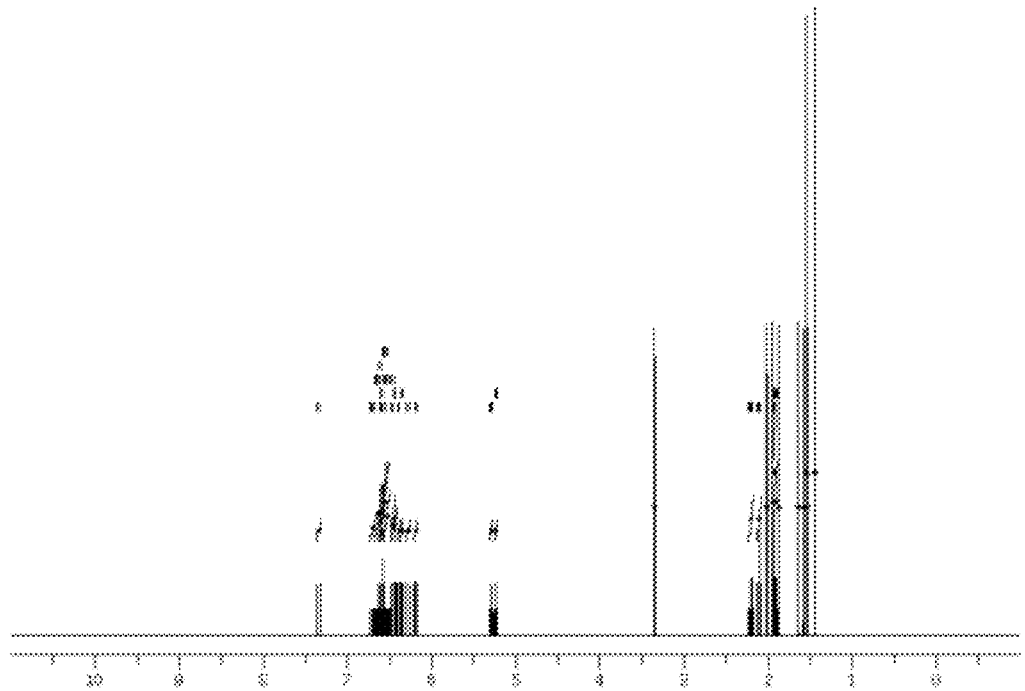
Figure 13D:
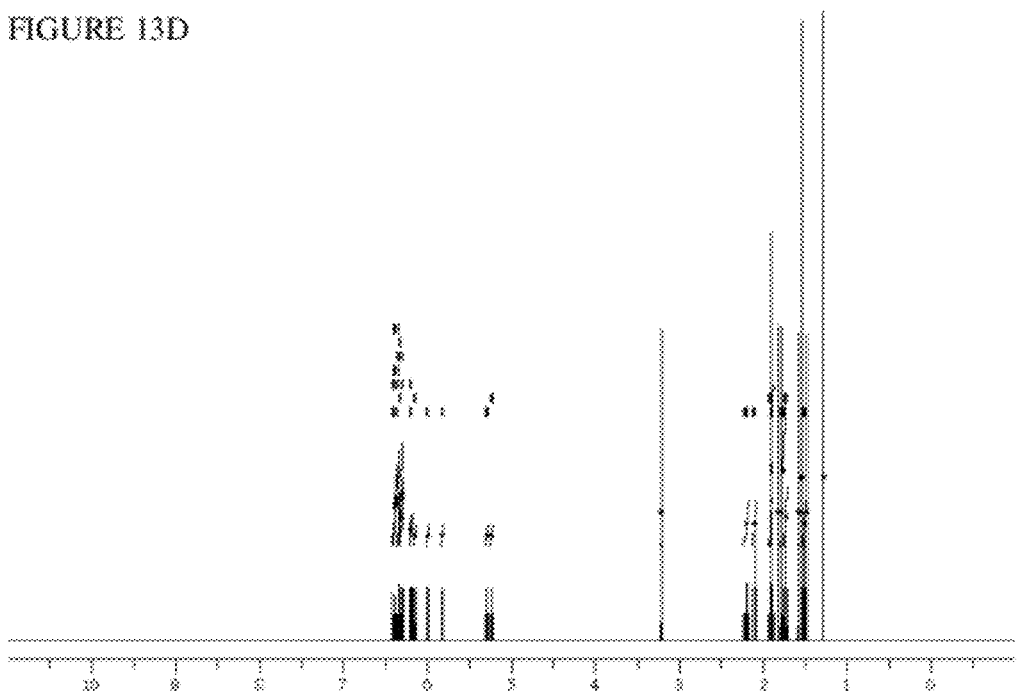

In addition, under condition without UV treatment, the Hs68 human fibroblasts were treated with 0.1, 0.5 and 10 μM lycopene (extracted from tomato) or 1, 5, 10 μM lycogen extract (extracted from photosynthetic bacteria of the present invention) for 24 hr. The type I procollagen level was analyzed by using Western blotting. As shown in FIG. 10, tomato extracted lycopene standard was unable to promote collagen proliferation (FIG. 10 (A)). However, the lycogen extract of the present invention was able to promote collagen proliferation in dose-dependent manner (FIG. 10 (B)).

Example 7

NMR Analysis

The sample used in the following was the ethanol acetone lycogen extract from the mutant photosynthetic bacteria of the present invention.
1. Sample Preparation About 15 mg sample was dissolved in D-chloroform. The resulted solution was loaded into conventional liquid-state NMR tube with loading volume about 500 μl. After the loading step, the tube was sealed with parafilm and stored under 4° C. Therefore, evaporation of the solvent and the degradation of the sample could be prevented.
2. NMR Experiment The prepared sample was put into liquid-state NMR machine (magnetic field intensity of 11.74 T, Varian) and spun with 20 rps to eliminate non-uniformity of the magnetic field and increase resolution of the spectrometer. The machine internal information of pulse sequence was called, and the $^1$H NMR, 1D $^{13}$C NMR, DEPT NMR, COSY NMR and NOESY NMR experiments were than conducted. The resulted spectrums were adjusted for their base line, phase and applied with window function. The objective of these adjustments was to make the following easier. One skilled in the art will recognize that these adjustments will not introduce distortion into the spectrums, and therefore wildly employed.
3. Spectrum Analysis The resulted $^1$H NMR spectrum, 1D $^{13}$C NMR spectrum, DEPT NMR spectrum, 2D COSY NMR spectrum (FIG. 14) and 2D NOESY NMR spectrum were analyzed. 1D $^{13}$C spectrum demonstrated all the $^{13}$C information. DEPT spectrum could be used to differentiate between methyl group, ethyl group and propyl group carbon atoms. COSY and NOSY spectrums were utilized to identify molecular structure.

The COSY spectrum was compared with predicted spectrums (FIG. 13, produced by NMR Predictor to identify components of the sample. To predict the NMR spectrums, the molecular profiles of compounds shown in FIG. 12 were downloaded from KEGG website and processed by NMR Predictor. The samples were qualitatively and quantitatively analyzed through information obtained from above-mentioned spectrums.

Figure 14:
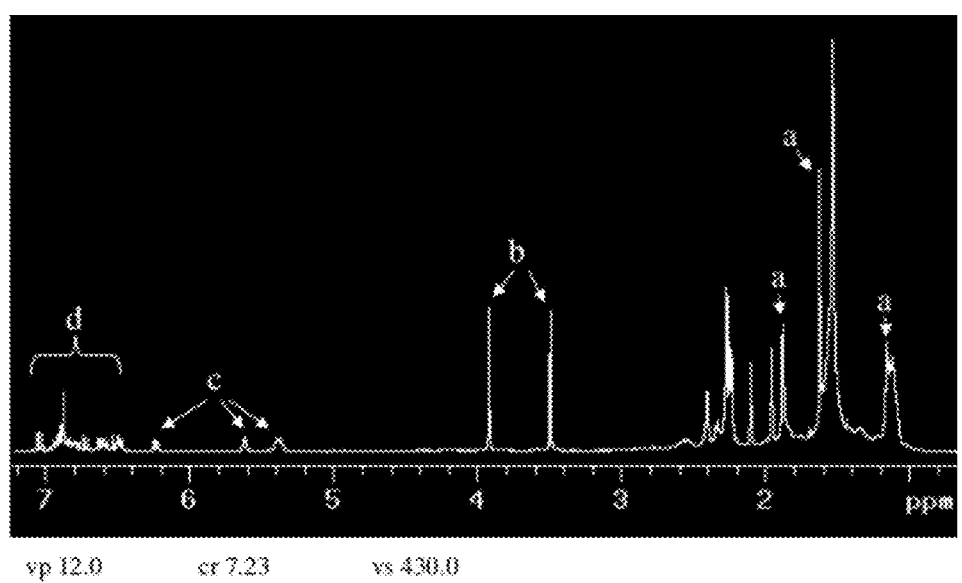
FIG. 14 shows the COSY NMR spectrum of the lycogen extract according to one embodiment of the present invention; peaks labeled with "a" represent possible impurities; peaks labeled with "b" represent spheriodenone and methoxyneurosporene; peaks labeled with "c" represent ζ-carotene and neurosporene; and peaks labeled with "d" represent spheriodenone.

Please refer to FIG. 14, peaks labeled with "a" represent possible impurities; peaks labeled with "b" represent spheriodenone and methoxyneurosporene; peaks labeled with "c" represent ζ-carotene and neurosporene; and peaks labeled with "d" represent spheriodenone. According to the low intensity of those peaks labeled with "c", relative to the two peaks between 3-4 ppm (peaks labeled with "b"), it can be concluded that spheroidenone and methoxyneurosporene are the major components of the sample with ratio of about 1:1. The spheroidenone is more than 30% by weight of the sample and the methoxyneurosporene is more than 30% by weight of the sample.

Figure 15A:
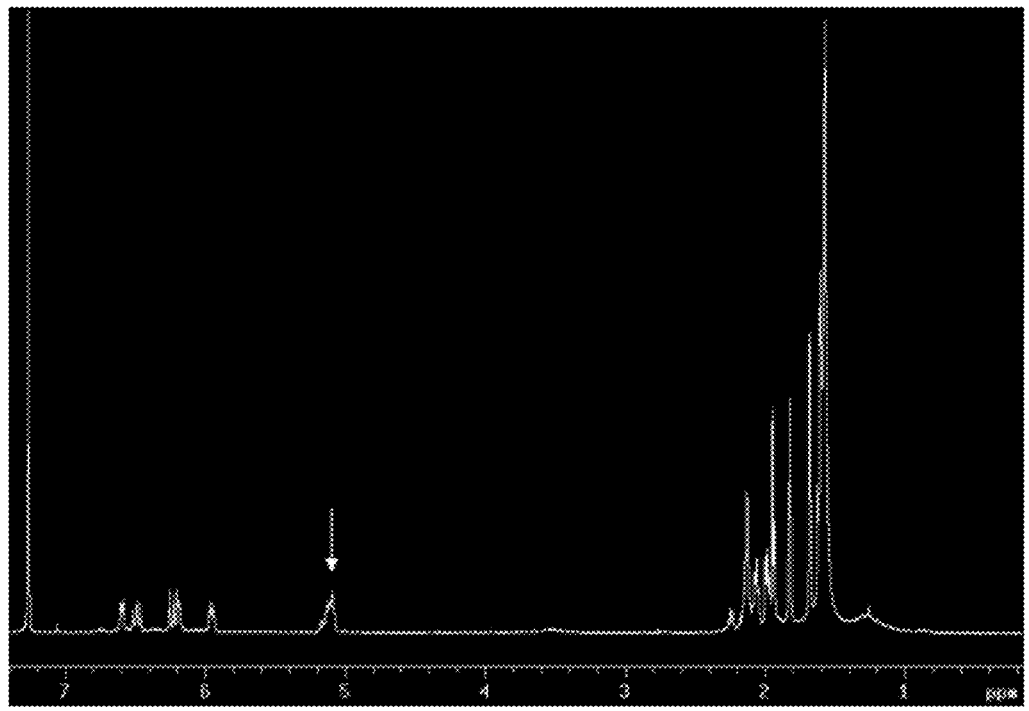
FIG. 15 shows the $^1$H NMR spectrums of the pure ζ-carotene (A) and pure neurosporene (B) according to one embodiment of the present invention; the arrows indicate peaks shown at 5.1 ppm in both spectrums.
Figure 15B:
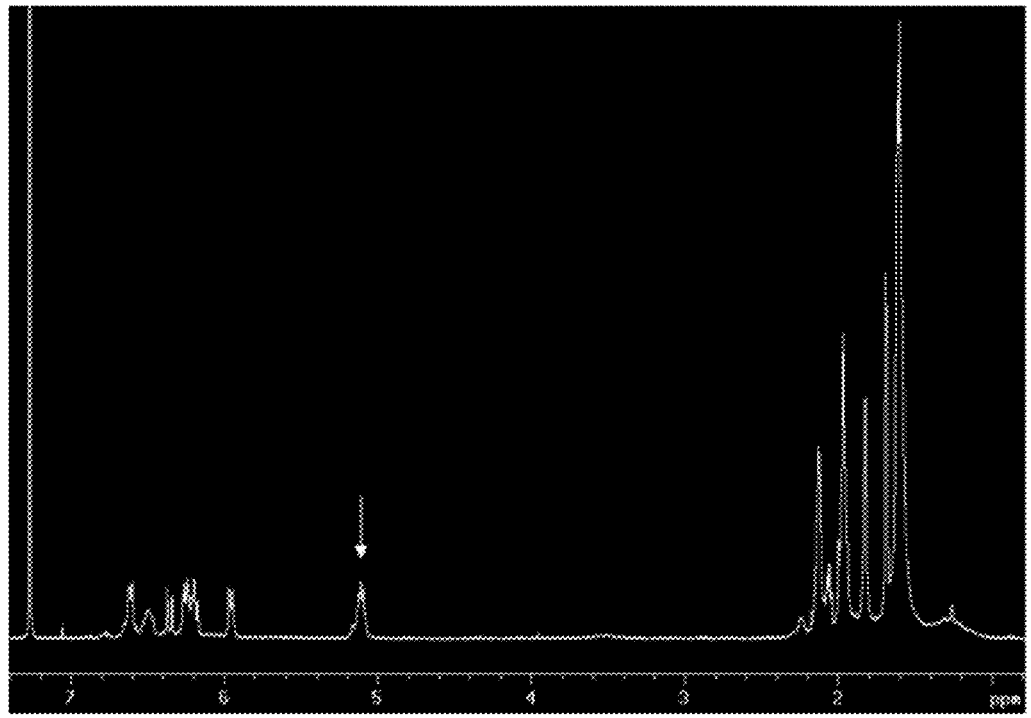
Figure 16A:
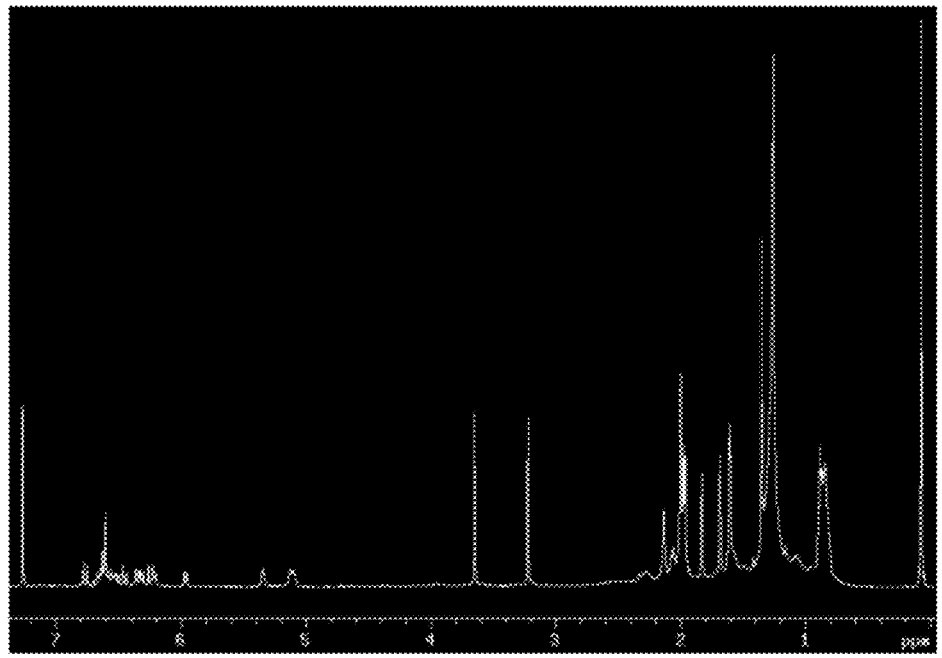
FIG. 16 shows the $^1$H NMR spectrums of the lycogen extract according to one embodiment of the present invention (A) and the enlargements (B and C).
Figure 16B:
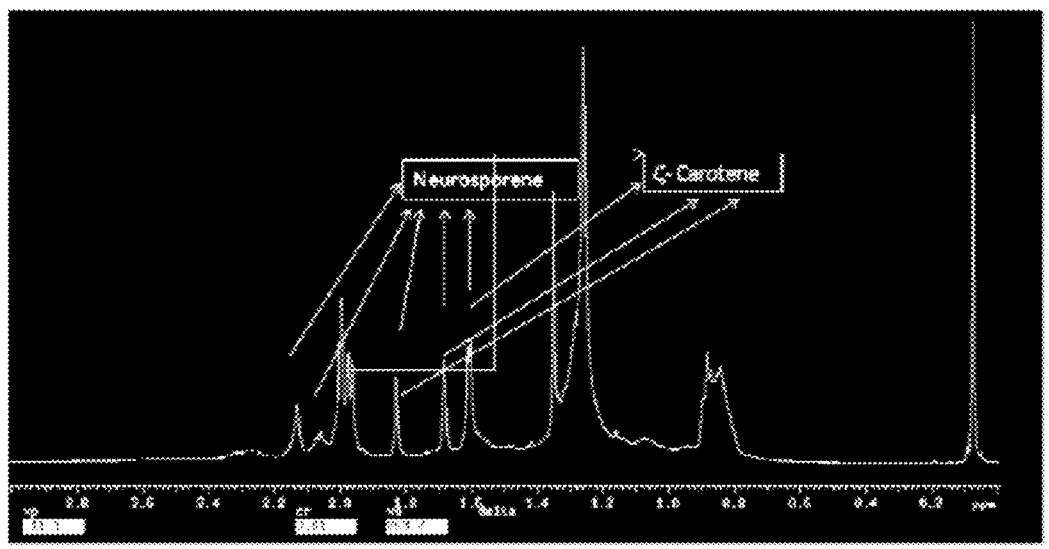
Figure 16C:
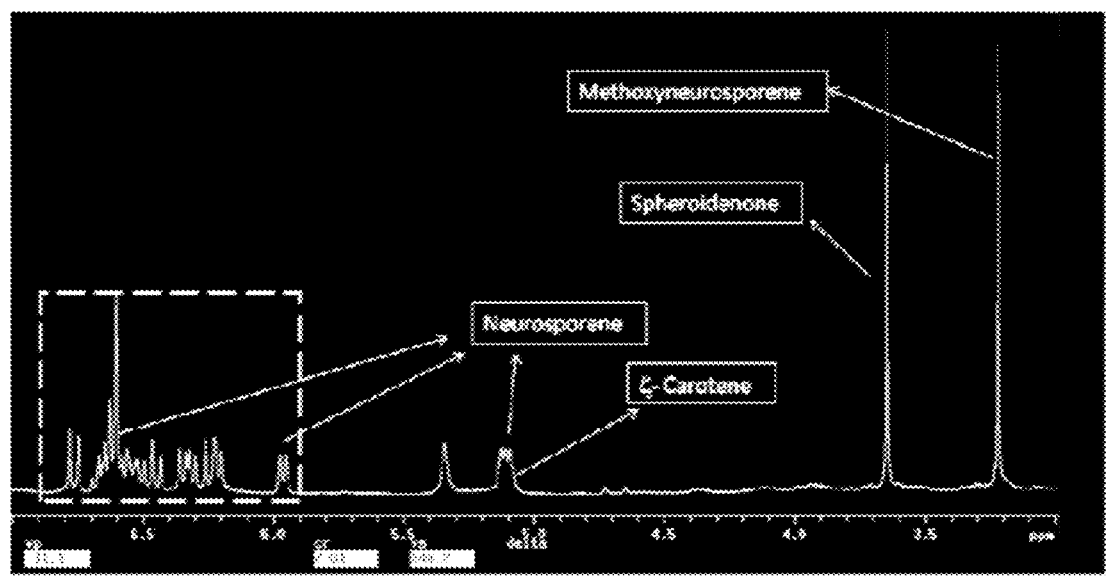
Figure 17:
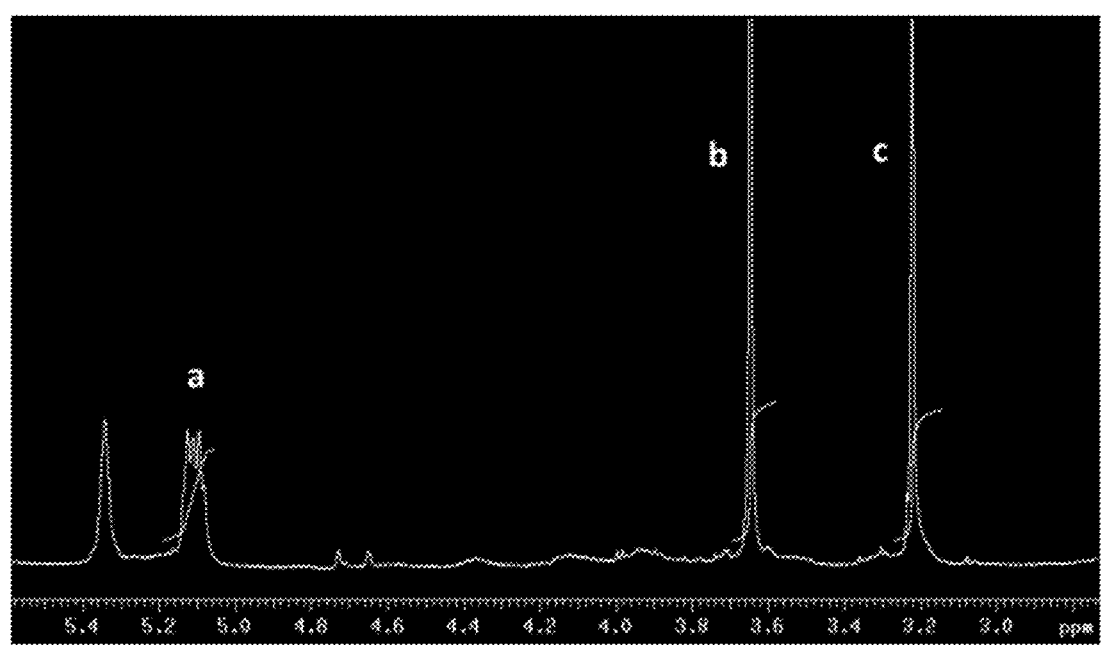
FIG. 17 shows the $^1$H NMR spectrums of the lycogen extract for quantitative analysis according to one embodiment of the present invention.

The pure ζ-carotene, pure neurosporene and lycogen extract were also subjected to the $^1$H NMR experiment. The resulted spectrums were shown in FIG. 15 to 17. Based on the previous mentioned information, the active ingredients of lycogen extract were further identified by comparing spectrum shown in FIG. 16 (A) and those shown in FIGS. 15 (A) and (B). The compounds to which each peaks of FIG. 16 (A) referred were labeled in FIGS. 16 (C) and (D). The peaks in rectangular area (dash line) of FIG. 16 (C) could be corresponded with those shown in spectrums of pure ζ-carotene and pure neurosporene (FIGS. 15 (A) and (B)). It had been found that both ζ-carotene and neurosporene generated peaks at 5.1 ppm, which were indicated by arrow in both FIGS. 15 (A) and (B).

The intensity of a peak and/or the area of a peak in NMR spectrum refer to quantity of the referenced compound. The ratio of intensity of arrow-pointed peaks shown in FIGS. 15 (A) and (B) was 1:1.273, which represents the ratio between ζ-carotene and neurosporene. The peak "a" in FIG. 17 was resulted from both ζ-carotene and neurosporene; the peak "b" was resulted from spheroidenone; and the peak "c" was resulted from methoxyneurosporene. The area ratio of a, b and c peaks shown in FIG. 17 was 1:1.553:1.604. According to all the above-mentioned data, it could be summarized that the quantity of ζ-carotene, neurosporene, spheroidenone and methoxyneurosporene were about 10.58%, 13.47%, 37.37% and 38.58% by weight of the lycogen extract respectively.

One skilled in the art readily appreciates that the present invention is well adapted to carry out the objects and obtain the ends and advantages mentioned, as well as those inherent therein. The animals, processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. An isolated strain of mutant photosynthetic bacteria, which is *Rhodobacter sphaeroides* with deposit number of DSM 25056, wherein the mutant photosynthetic bacteria comprises DNA sequence as shown in SEQ ID NO:1 for CrtC enzyme (hydroxyneurosporene dehydrogenase).

2. A lycogen extract which is extracted from *Rhodobacter sphaeroides* with deposit number of DSM 25056 comprising active ingredient of ζ-carotene, neurosporene, spheroidenone and/or methoxyneurosporene.

3. The extract of claim 2, wherein the ζ-carotene is more than 10% by weight of the lycogen extract.

4. The extract of claim 2, wherein the neurosporene is more than 10% by weight of the lycogen extract.

5. The extract of claim 2, wherein the spheroidenone is more than 30% by weight of the lycogen extract.

6. The extract of claim 2, wherein the methoxyneurosporene is more than 30% by weight of the lycogen extract.

7. A composition for anti-inflammation, anti-oxidation, skin lightening, inhibiting collagen degradation or increasing collagen production, comprising the extract of claim 3 and food scientific or pharmaceutical acceptable carrier.

8. The composition of claim 7, which is in a form of food supplement, animal feed, human food product or pharmaceutical or cosmetic composition.

* * * * *

SEQUENCE LISTING

<160> NUMBER OF SEQ ID NOS: 4

<210> SEQ ID NO 1
<211> LENGTH: 840
<212> TYPE: DNA
<213> ORGANISM: Rhodopseudomonas palustris
<220> FEATURE:
<221> NAME/KEY: gene
<222> LOCATION: (1)..(840)

<400> SEQUENCE: 1

```
tcaggaaaag ctccagccgg ggcggcgggg gacgcggacg gcgagcatcg gcatcaggag      60
cggcgagcgg aagcgacgca gatcgagcgc ctcgtgcacg ccgaccgtct tctggccgaa     120
gaccgtcgtc tcgaccatcg cgcgcgaata gaagggcgcg tcgagcatcg acatcacctg     180
ccgcggccgt gtgcccggat cggcgggcgt gtgacgctcg accagccagc gcgagcgggc     240
gaagcgggct tcgggcggcg gctggatcag ccgggcgcgc cggtcggccg cgacatggag     300
cccgagctca agccgggagc cgtcgcggcg ggtcgcgtcg tagaagcagg ccgccccgtc     360
tgccaccggg tagcggcccc aggtccagaa acggaagtcg gcctcgagcg cggccgtgcc     420
gaaattggca tcgaaatagc cgtggccgtg ccagcggtgg ccctgcgtca gatcgacctc     480
gatgcgcgcg gtggggcgga aggggcgcca gatgtgcgag ccatcgtcct tgagcgtcac     540
ctcgacatcg gtgatcccgg tggggtcag cacgatccgg cccttcaccg gcgagacgag     600
gggcggcgag gagatctcgt tcacctcgac gatgagctgg gtgccggtcc agtgcatccg     660
cgagggcccc acggtcagcg tgtccgggct ctggcgcagc gcggcgcggc cgcggtcggt     720
catggtgaag cgcccgccgg ggccgtaggt cgccacattg aggcagcagt ggttctgcgg     780
ctccttccgg cccgaccagc gataccaggg cgagaagacc gagccgatga agccgatcac     840
```

<210> SEQ ID NO 2
<211> LENGTH: 293
<212> TYPE: PRT
<213> ORGANISM: Rhodobacter sphaeroides
<220> FEATURE:
<221> NAME/KEY: MUTAGEN
<222> LOCATION: (1)..(293)

<400> SEQUENCE: 2

```
Val Ile Gly Phe Ile Gly Ser Val Phe Ser Pro Trp Tyr Arg Trp Ser
1               5                   10                  15

Gly Arg Lys Glu Pro Gln Asn His Cys Cys Leu Asn Val Ala Thr Tyr
            20                  25                  30

Gly Pro Gly Gly Arg Phe Thr Met Glu Thr Thr Asp Arg Gly Arg Ala
        35                  40                  45

Ala Leu Arg Gln Ser Pro Asp Thr Leu Thr Val Gly Pro Ser Arg Met
    50                  55                  60

Glu Thr His Trp Thr Gly Thr Gln Leu Ile Val Glu Val Asn Glu Ile
65                  70                  75                  80

Ser Ser Pro Pro Leu Val Ser Pro Val Lys Gly Arg Ile Val Leu Thr
                85                  90                  95

Pro Thr Gly Ile Thr Asp Val Glu Val Thr Leu Lys Asp Asp Gly Ser
            100                 105                 110

His Ile Trp Arg Pro Phe Ala Pro Thr Ala Arg Ile Glu Val Asp Leu
        115                 120                 125

Thr Gln Gly His Arg Trp His Gly His Gly Tyr Phe Asp Ala Asn Phe
    130                 135                 140
```

Gly Thr Ala Ala Leu Glu Ala Asp Phe Arg Phe Trp Thr Trp Gly Arg
145                 150                 155                 160

Tyr Pro Val Ala Asp Gly Ala Ala Cys Phe Tyr Asp Ala Thr Arg Arg
                165                 170                 175

Asp Gly Ser Arg Leu Glu Leu Gly Leu His Val Ala Ala Asp Arg Arg
            180                 185                 190

Ala Arg Leu Ile Gln Pro Pro Glu Ala Arg Phe Ala Arg Ser Arg
        195                 200                 205

Trp Leu Val Glu Arg His Thr Pro Ala Asp Pro Gly Thr Arg Pro Arg
    210                 215                 220

Gln Val Met Glu Thr Ser Met Glu Thr Leu Asp Ala Pro Phe Tyr Ser
225                 230                 235                 240

Arg Ala Met Glu Thr Val Glu Thr Thr Val Phe Gly Gln Lys Thr Val
                245                 250                 255

Gly Val His Glu Ala Leu Asp Leu Arg Arg Phe Arg Ser Pro Leu Leu
            260                 265                 270

Met Glu Thr Pro Met Glu Thr Leu Ala Val Arg Val Pro Arg Arg Pro
        275                 280                 285

Gly Trp Ser Phe Ser
    290

<210> SEQ ID NO 3
<211> LENGTH: 955
<212> TYPE: DNA
<213> ORGANISM: Rhodobacter sphaeroides
<220> FEATURE:
<221> NAME/KEY: gene
<222> LOCATION: (1)..(955)

<400> SEQUENCE: 3 aaaaggggggg ggctgtctgc ccccccttgcc cctgcggggc aattccccccc gaggatatttt    60
gcgcagagtg aaaggcgcgg ccggcggcgg ccgggatgtc aggaaaagct ccagccgggg    120
cggcggggga cgcggacggc gagcatcggc atcaggagcg gcgagcggaa gcggcgcaga    180
tcgagagcct cgtgcacgcc gaccgtcttc tggccgaaga ccgtcgtctc gaccatcgcg    240
cgcgcataga agggcgcgtc gagcatcgac atcacctgcc gcggccgtgt gcccggatcg    300
gcgggcgtgt ggcgctcgac cagccagcgc gagcgggcga agcgggcttc gggcggcggc    360
tggatcagcc gcgcgcgccc gtcggccgcg acatggagcc cgagctcgag ccgggagccg    420
tcgcggcggg tcgcgtcgta gaagcaggcc gccccgtctg ccaccgggta gcggccccag    480
gtccagaaac ggaagtcggc ctcgagcgcg gccgtgccga aattggcatc gaaatagccg    540
tggccgtgcc agcggtggcc ctgcgtcaga tcgacctcga tgcgcgcggt gggtgcgaag    600
gggcgccaga tgtgcgagcc atcgtccttg agcgtcacct cgacatcggt gatcccggtg    660
ggggtcagca cgatccggcc cttcaccggc gagacgaggg cggcgaggga gatctcgttc    720
acctcgacga tgagctgggt gccggtccag tgcatccgcg aggggcccac ggtcagcgtg    780
tccgggctct gccgcagcgc ggcggccgcg tcggtcatgg tgaagcgccc gccggggccg    840
taggtcgcca cattgaggca gcagtggttc tgcggctcct tccggcccga ccagcgatac    900
cagggcgaga agaccgagcc gatgaagccg atcaccgaga gcgcgcggtg ccgtc    955

<210> SEQ ID NO 4
<211> LENGTH: 278
<212> TYPE: PRT
<213> ORGANISM: Rhodobacter sphaeroides
<220> FEATURE:

-continued

```
<221> NAME/KEY: INIT_MET
<222> LOCATION: (1)..(278)

<400> SEQUENCE: 4

Met Ile Gly Phe Ile Gly Ser Val Phe Ser Pro Trp Tyr Arg Trp Ser
1               5                   10                  15

Gly Arg Lys Glu Pro Gln Asn His Cys Cys Leu Asn Val Ala Thr Tyr
            20                  25                  30

Gly Pro Gly Gly Arg Phe Thr Met Thr Asp Ala Ala Ala Leu Arg
        35                  40                  45

Gln Ser Pro Asp Thr Leu Thr Val Gly Pro Ser Arg Met His Trp Thr
    50                  55                  60

Gly Thr Gln Leu Ile Val Glu Val Asn Glu Ile Ser Ser Pro Pro Leu
65                  70                  75                  80

Val Ser Pro Val Lys Gly Arg Ile Val Leu Thr Pro Thr Gly Ile Thr
                85                  90                  95

Asp Val Glu Val Thr Leu Lys Asp Asp Gly Ser His Ile Trp Arg Pro
                100                 105                 110

Phe Ala Pro Thr Ala Arg Ile Glu Val Asp Leu Thr Gln Gly His Arg
            115                 120                 125

Trp His Gly His Gly Tyr Phe Asp Ala Asn Phe Gly Thr Ala Ala Leu
    130                 135                 140

Glu Ala Asp Phe Arg Phe Trp Thr Trp Gly Arg Tyr Pro Val Ala Asp
145                 150                 155                 160

Gly Ala Ala Cys Phe Tyr Asp Ala Thr Arg Arg Asp Gly Ser Arg Leu
                165                 170                 175

Glu Leu Gly Leu His Val Ala Ala Asp Gly Arg Ala Arg Leu Ile Gln
            180                 185                 190

Pro Pro Pro Glu Ala Arg Phe Ala Arg Ser Arg Trp Leu Val Glu Arg
        195                 200                 205

His Thr Pro Ala Asp Pro Gly Thr Arg Pro Arg Gln Val Met Ser Met
    210                 215                 220

Leu Asp Ala Pro Phe Tyr Ala Arg Ala Met Val Glu Thr Thr Val Phe
225                 230                 235                 240

Gly Gln Lys Thr Val Gly Val His Glu Ala Leu Asp Leu Arg Arg Phe
                245                 250                 255

Arg Ser Pro Leu Leu Met Pro Met Leu Ala Val Arg Val Pro Arg Arg
            260                 265                 270

Pro Gly Trp Ser Phe Ser
            275
```